United States Patent
Henschke et al.

(10) Patent No.: US 8,648,188 B2
(45) Date of Patent: Feb. 11, 2014

(54) PREPARATION OF 2-CHLORO-9-(2'-DEOXY-2'-FLUORO-β-D-ARABINOFURANOSYL)-ADENINE

(75) Inventors: Julian Paul Henschke, Summertown (AU); Xiaoheng Zhang, Lianyungana (CN); Lijun Mei, Taihe County (CN); Yung-Fa Chen, Tainan (TW)

(73) Assignee: Scinopharm Taiwan, Ltd., Tainan (TW)

( * ) Notice: Subject to any disclaimer, the term of this patent is extended or adjusted under 35 U.S.C. 154(b) by 285 days.

(21) Appl. No.: 13/179,259

(22) Filed: Jul. 8, 2011

(65) Prior Publication Data
US 2012/0010397 A1    Jan. 12, 2012

(30) Foreign Application Priority Data
Jul. 9, 2010 (CN) .......................... 2010 1 0224898

(51) Int. Cl.
*C07H 19/00* (2006.01)
*C07H 19/19* (2006.01)

(52) U.S. Cl.
USPC ...................................... 536/27.11; 536/27.4

(58) Field of Classification Search
None
See application file for complete search history.

(56) References Cited

U.S. PATENT DOCUMENTS

| | | | |
|---|---|---|---|
| 4,751,221 A | 6/1988 | Watanabe et al. | |
| 4,918,179 A * | 4/1990 | Watanabe et al. | 536/27.4 |
| 5,602,246 A | 2/1997 | Bauman et al. | |
| 6,680,382 B2 | 1/2004 | Bauta et al. | |
| 6,949,640 B2 | 9/2005 | Montgomery et al. | |
| 7,470,784 B2 | 12/2008 | Montgomery et al. | |

FOREIGN PATENT DOCUMENTS

| WO | WO90/14352 | 11/1990 |
|---|---|---|
| WO | WO03/011877 | 2/2003 |

OTHER PUBLICATIONS

Pankiewiez, et al., A Synthesis of 9-(2-Deoxy-2-fluoro-B-D-arabinofuranosyl)adenine and Hypoxanthine. An effect of C3-Endo to C2'-Endo conformational shift on the reaction course of 2'-hydroxyl group with DAST, J. Org. Chem (1992) XP0002107309.
Alauddin, et al., Synthesis of [18F]-labeled adenosine analogues as potential PET Imaging agents, J. Label Compounds and Radiopharmaceuticals (2003) 46: 805-814 XP002542958.
Takamatsu, et al., Improved synthesis of 9-(2,3-dideoxy-2-fluro-B-D-threo-pentofuranosyl)adenine (FddA) using triethlamine trihydrofluoride. Tetrahedron Letters 42: 2321-2324 (2001).
Extended European Search Report dated Oct. 28, 2011.
Montgomery et al., Synthesis and Biologic Activity of 2'-Fluoro-2-halo Derivatives of 9-β-D-Arabinofuranosyladenine, *J. Med. Chem*, vol. 35, pp. 397-401 (1992).
Anderson et al., Potential Anticancer Agents. VII. Synthesis Ammonolysis of Methyl 2,3-Anhydro-D-ribofuranoside, J. Am. Chem. Soc., 80, (1958) pp. 5247-5252.
Ishido et al., Partial Protection of Carbohydrate Derivatives. Part 3. Regioselective 2'-O-Deacylation of Fully Acylated Purine and Pyrimideine Ribonucleosides with Hydrazine Hydrate, *J.C.S. Perkin I*, (1979) pp. 2088-2098.
Ishido et al., Partial Protection of Carbohydrate Derivatives. Part 4. Regioselective 2'-O-Deacylation of Fully Acylated Purine and Pyrimideine Ribonucleosides with Hydroxylaminium Acetate, *J.C.S. Perkin I*, (1980) pp. 563-573.
Montogmery et al., 9-(2-Deoxy-2-fluoro-beta.-D-arabinofuranosyl)guanine: a metabolically stable cytotoxic analogue of 2;-deoxyguanosine, *J. Med. Chem*. (1986), pp. 2389-2392.
Wright et al., Nucleosides. LX. Fluorocarbohydrates. 22. Synthesis of 2-deoxy-2-fluoro-D-arabinose and 9-(2-deoxy-2-fluoro-.alpha. and .beta.-D-arabinofuranosyl)adenines, *J. Org. Chem*. vol. 34, pp. 2632-2636 (1969).

(Continued)

*Primary Examiner* — Lawrence E Crane
(74) *Attorney, Agent, or Firm* — Enshan Hong; Kent H. Cheng; VLP Law Group LLp

(57) ABSTRACT

A process for making clofarabine comprising: fluorinating a compound of formula VII

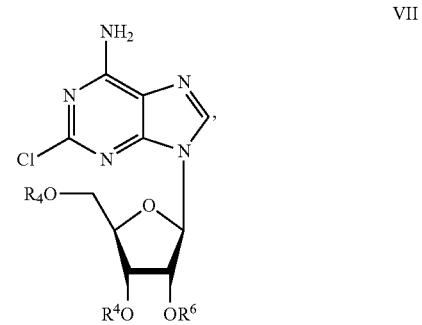

wherein each $R^4$ is independently a hydroxy protecting group, $OR^6$ is a leaving group, with a fluorinating agent in the presence of guanidine carbonate to give a compound of formula VIII:

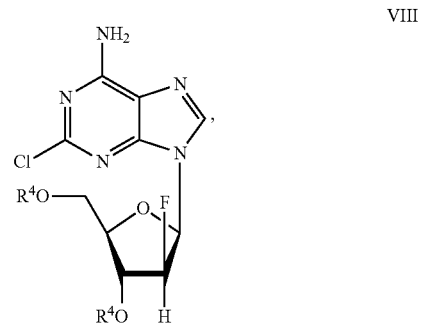

wherein $R^4$ is as defined above; and deprotecting the compound of formula VIII to give the clofarabine.

25 Claims, No Drawings

(56) References Cited

OTHER PUBLICATIONS

Brodfuehrer et al., A stereocontrolled synthesis of 1,3,5-tri-O-benzoyl-.alpha.-D-ribofuranose, *J. Org. Chem.* pp. 2597-2598 (1985).

Tann et al., Fluorocarbohydrates in Sythesis. An efficient synthesis of 1-(2-Deoxy-2-fluoro-β-D-arabino-furanosyl)-5-iodouracil (β-FIAU) and 1-(2-Deoxy-2-fluor-β-D-arabinofuranosyl)thymine (β-FMAU), *J. Org. Chem.* (1985) pp. 3644-3647.

Howell et al., Antiviral Nucleosides. A Stereospecific, Total Synthesis of 2'-Fluoro-2'-deoxy-β-D-arabinofuranosyl Nucleosides, *J. Org. Chem.* pp. 85-88 (1988).

Sakairi et al., Partial Protection of Carbohydrate Derivatives. Part 2. Equilibration between 2', 5'-and 3', 5'-Di-O-Benzoyladenosine Derivatives Substituted at the $N^6$-Position, on Silica Gel, *Nucleosides & Nucleotides*, 1(2), 99-110 (1982).

Bauta et al., A New Process for Antineoplastic Agents Clofarabine, *Organic Process Research & Development*, pp. 889-896, (2004).

Ishido et al., Equilibration between 3',5'- and 2',5'-di-O-acylribonucleosides on silica el in the region-selective 2'-O-deacylation of fully acylated ribonucleosides, Nucleic Acids Research, pp. 263-265.

McClinton, Martin, Triethylamine Tris(hydrogen fluoride): Applications in Synthesis, *Aldrichimica Acta*, vol. 28, No. 2 (1995).

Yoneda, Norihiko, The combination of hydrogen fluoride with organic bases as fluorination agents, *Tetrahedron* vol. 47, No. 29, pp. 5329-5365 (1991).

\* cited by examiner

PREPARATION OF 2-CHLORO-9-(2'-DEOXY-2'-FLUORO-β-D-ARABINOFURANOSYL)-ADENINE

RELATED APPLICATIONS

This application claims priority from China Patent Application No. 201010224898.2 filed Jul. 9, 2010.

BACKGROUND OF THE INVENTION

1. Field of the Invention

The present application relates to process of making clofarabine, which is an active pharmaceutical ingredient.

2. Description of the Related Art

Clofarabine is the active pharmaceutical ingredient (API; drug substance) in the anticancer drug product Clolar®, which was originally developed by Ilex Oncology. Clolar® was approved for sale by the FDA in 2004 for treating children with refractory or relapsed acute lymphoblastic leukemia. Clofarabine is a fluoro-deoxy arabinonucleoside, which is a synthetic analogue of adenosine.

Wright et al.[1] reported the synthesis of 9-(2-deoxy-2-fluoro-β-D-arabinofuranosyl)-adenine (1), which is simply the 2-dechloro analogue of clofarabine, by acid catalysed (p-TsOH) fusion (coupling) of 1,3-di-O-acetyl-5-β-benzyl-2-deoxy-2-fluoro-D-arabinofuranside (2), which was prepared from methyl 2,3-anhydro-α-D-ribofuranoside (3),[2] with 2,6-dichloropurine (4) (notice that this is the free purine, i.e., it is not silylated or deprotonated) to give a 30% isolated yield of β-N9 and 29% α-N9 by short column chromatography, followed by amination and reduction reaction (Scheme 2). An important aspect and disadvantage to this process is the fact that a 1:1 mixture of α- and β-anomers are formed (only the β-anomer is desired) and the follow-on effect from this is that column chromatography is needed to separate the isomers. This makes such a process not amenable to scale-up due to the cost of large scale-up chromatography. Another aspect of note is that the choice of benzyl protection of the C5'-OH meant that the process could not be used to synthesize clofarabine because hydrogenolysis of benzyl group leads to simultaneous removal of the requisite C2-chlorine atom on the adenine ring. That is, benzyl groups and the chlorine atom of the adenine ring are not orthogonal. Thus, the starting material 2 could not be used to synthesize clofarabine.

Watanable et al.[3] disclose a synthesis approach to 2'-deoxy-2'-fluoro-arabinofuranosyl purine nucleosides under solution conditions without a catalyst utilizing 2 as a starting material, but clofarabine was not accessible using this route.

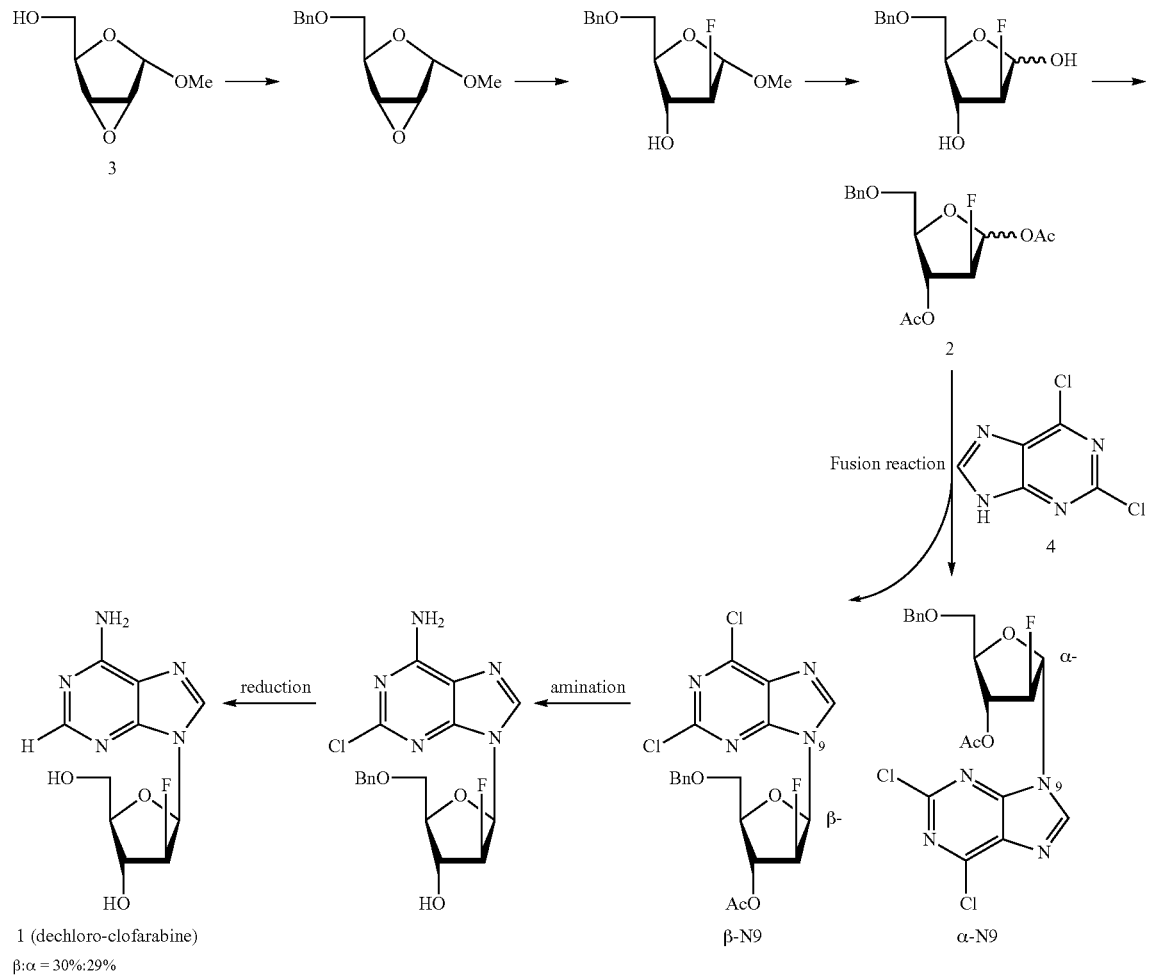

Scheme 2 - Wright et al.'s 1969 approach to dechloro-clofarabine 1 (dechloro-clofarabine)
β:α = 30%:29%

Perhaps in an effort to solve this problem, Reichman et al.[4] synthesized 3-O-acetyl-5-O-benzoyl-2-deoxy-2-fluoro-β-D-arabinofuranosyl bromide (5a), by a long multi-step procedure (Scheme 3), which instead exchanged the troublesome benzyl group for a benzoyl group.

mediate 5a, and therefore in lower yield based on the true carbohydrate starting material. The authors also tested the 1-O—Ac-desbromo analogue 5b in the coupling with 4 but this did not provide an acceptable yield of the desired β-anomer of 6.

Scheme 3 - Reichman's synthesis of 1-bromo-2-fluoro-arabinofuranose 5

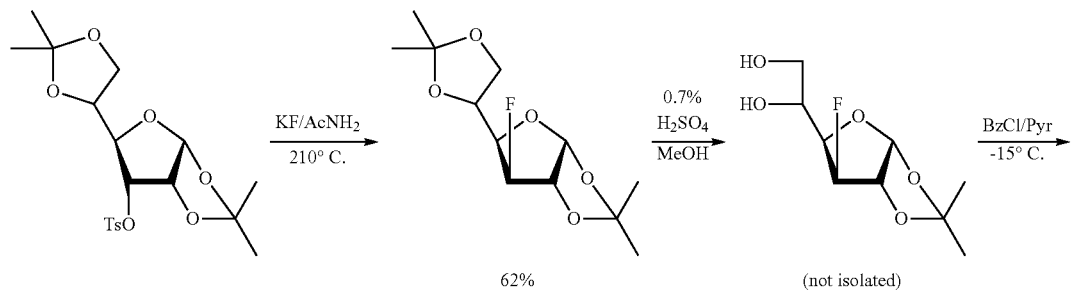

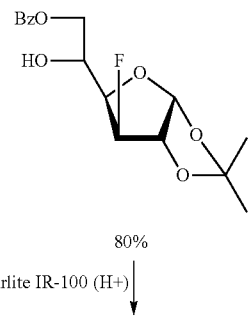

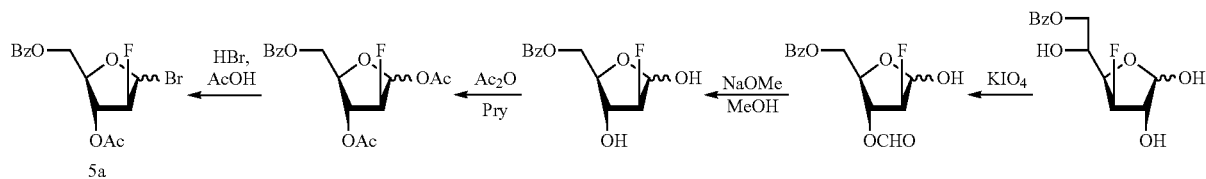

Montgomery et al.[5] later successfully utilized this differently protected 1-α-bromo carbohydrate 5a in the synthesis of protected dichloropurine-based nucleoside 6 through the coupling of free 2,6-dichloropurine (4) in DCE in at 100° C. over a 16-hour period in the presence of molecular sieves (Scheme 4). Although the desired β-anomer of 6 was the major product other nucleosides including the β-anomer of 6 were also formed, once again showing pre-fluorination of the carbohydrate ring leads to an inherently inefficient coupling step. Pure protected nucleoside 6 was only obtained after the purification by column chromatography in 32% yield from inter- Scheme 4 - Montgomery's synthesis of a dichloropurine-based protected nucleoside

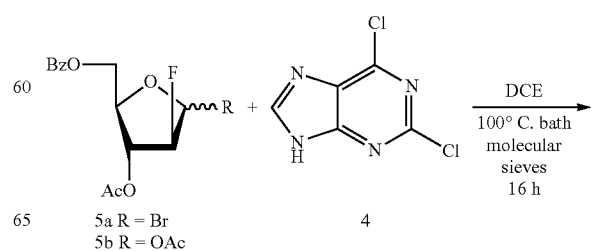

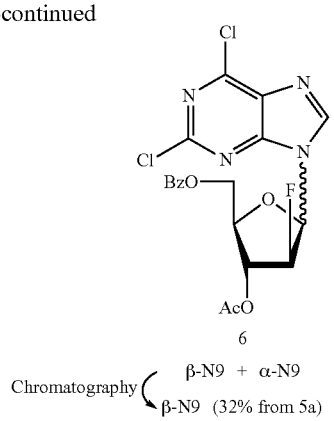

6

Chromatography ( β-N9 + α-N9
β-N9 (32% from 5a)

At the same time that Montgomery utilized 1-α-bromo sugar 5a as a starting material in the synthesis of dichloropurine nucleoside 6 (above), Howell et al.[6] instead utilized the close analogue 2-deoxy-2-fluoro-3,5-di-O-benzoyl-α-D-arabino-furanosyl bromide (8) (Scheme 5). These two compounds, viz. 5a and 8, differ only by the acyl protecting group positioned at C3-0. Howell et al.'s bromosugar 8 was prepared in 4 synthetic steps in 33-43% overall yield (43% if a recycle is used) from 1-O-acetyl-2,3,5-tri-O-benzoyl-β-D-ribofuranose (9; which is the same starting material as used in our synthesis of clofarabine) using rearrangement, sulfonylation, fluorination, and finally bromination steps (Scheme 5). This bromosugar 8 has since been the key starting material in most clofarabine syntheses that we are aware of, but can also be used in the synthesis of other nucleosides such as a series of (2'-fluoro-2'-deoxy-β-D-ribofuranosyl)-uracils 10a-d.[7]

Montgomery was the first to disclose a method for the synthesis of clofarabine (7).[8] The method comprised using his already disclosed[7] uncatalysed coupling of 1-α-bromo sugar 5a with 2,6-dichloropurine (4), followed by a dual amination and deprotection step (Scheme 6). The coupling reaction of 4 and 5a at reflux in DCE gave an anomeric mixture of N9 isomers from which the desired N9 β-anomer isomer of intermediate 6 was obtained in 32% yield after column chromatography. Amination and deprotection of the desired N9 β-anomer of 6 gave clofarabine (7). Amination by itself provided a mono-benzoylated clofarabine intermediate (i.e., amination only deprotected the C3'-OAc group and substituted the C6-Cl group) which had to be further deprotected by the addition of LiOH to give 7. Three recrystallization from water gave pure 7 in 42% yield. The overall yield of clofarabine was only 13% based on 5a, and therefore in lower yield based on the carbohydrate starting material that was used to make 5a itself.

Not only was the longwinded purification of 6 and 7 not fit for commercial production on scale-up, but the synthesis of the starting material carbohydrate 5a[6] was complicated. Moreover, the instability of 5a was also a disadvantage for scale-up and the coupling reaction had to be run under very dry (i.e., low levels of water) conditions, since otherwise 5a partially decomposed during the reaction.

Scheme 5 - Howell's synthesis of uracil-based nucleosides

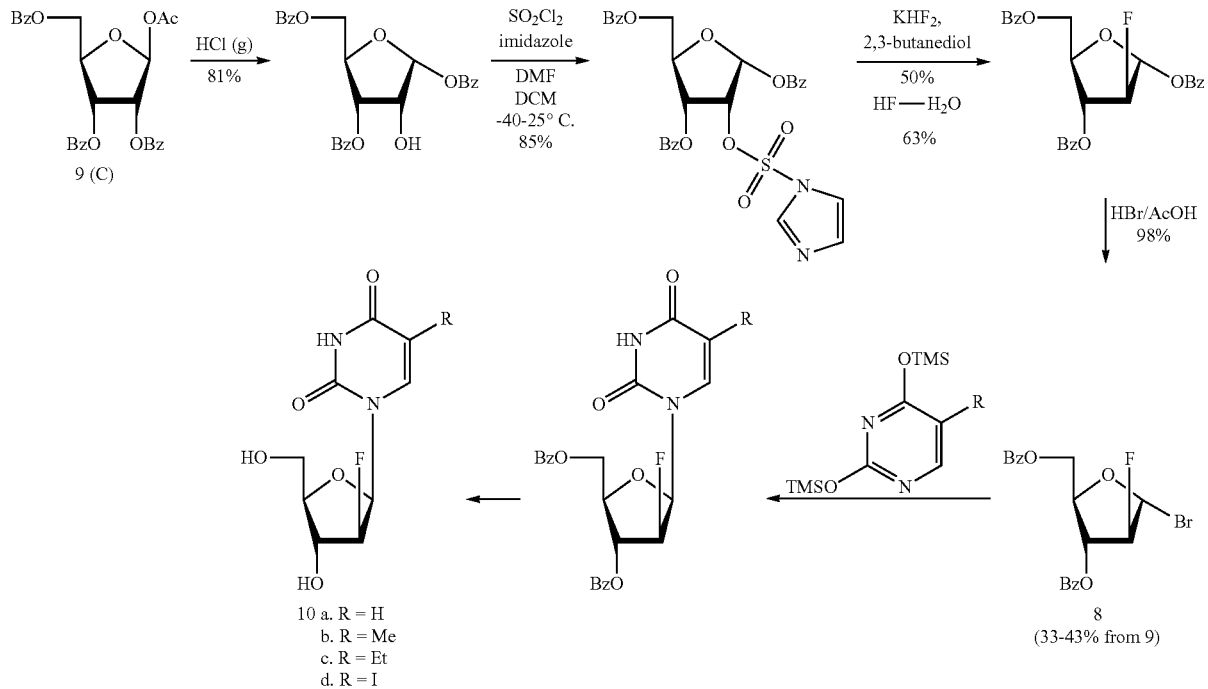

10 a. R = H
b. R = Me
c. R = Et
d. R = I 8
(33-43% from 9)

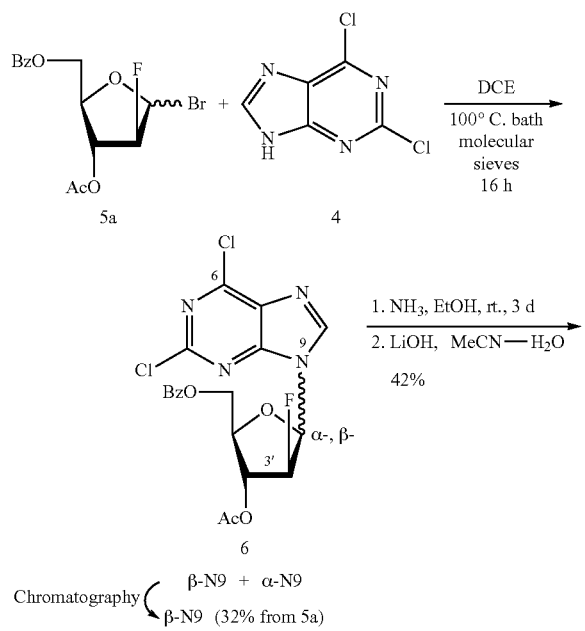

Scheme 6 - The first synthesis of clofarabine, by Montgomery

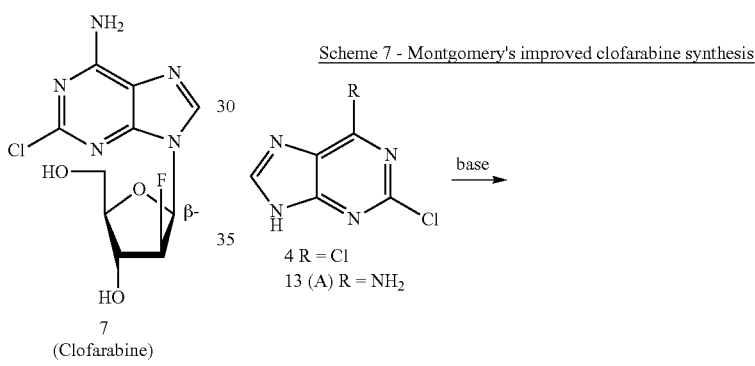

Much more recently, Montgomery reported an improved method that involved the coupling of the sodium salt 17, or other salts (such as formed using DBU), of 2-chloro-6-substituted purine (due to the relatively high acidity of the N9 hydrogen) with the now preferred 2-deoxy-2-fluoro-3,5-di-O-benzoyl-α-D-arabinofuranosyl bromide (8) to give an anomeric mixture of intermediate 11 (Scheme 7).[9] One key and obvious difference between this and the older procedure was the use of an anionic salt of the purine, which would function to render it more reactive. Indeed, the coupling reaction could be conducted at room temperature rather than at 100° C. It can be seen that intermediate 11 is a close analogue of the intermediate used in Montgomery's first synthesis of clofarabine. The N9 β-anomer of 11 was separated from the N9 α-anomer by a flash column and crystallized from ethanol and chloroform in almost 70% yield. The product was contaminated with a small amount of the α-anomer. Thus, it is clear the breakthrough with this procedure which leads to the much higher yield of the β-anomer being formed was a result of utilizing an $S_N2$ reaction in the coupling step rather than $S_N1$. Because it was difficult to remove the benzoyl groups with ammonia, sodium methoxide was used instead prior to the amination. This resulted in the halogen positioned at C6 being substituted with a methoxy group to give compound 12, in 80% yield. Amination with ammonia displaced the methoxy group to give clofarabine (7) in 78% yield. As a result of using an $S_N2$ approach to the coupling step, the yield was improved to 47% based on carbohydrate 8, which is an overall yield of up to 18% from 8.

Although a halogen atom positioned at C6 was preferred, they also claimed alkoxy, azido, amino and protected amino groups at this position. Thus, 2-chloroadenine (13) converted to its DBU salt derivative could be coupled with 8 but this was only demonstrated on a very small scale and the yield of N9 β-anomer of 14, as isolated following preparative TLC, was a low 28%.

Despite these improvements, the main drawback of this process, being that the anomeric mixture of intermediates required column chromatography for their separation, still remained. Also the patent examples did not demonstrate that this procedure was applicable to large scale manufacture of clofarabine.

Scheme 7 - Montgomery's improved clofarabine synthesis

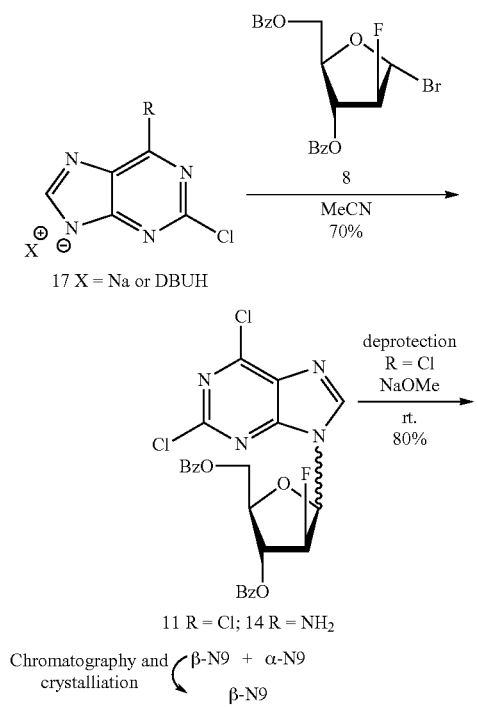

Researchers at ILEX Products, Inc. and Ash Stevens, Inc. optimized the above discussed Montgomery procedures using the potassium salt 11 of 2-chloro-6-aminopurine (a.k.a., 2-chloroadenine; 13), instead of the sodium salts of 2,6-dichloropurine (4), in the coupling with the same bromocarbohydrate 8 in a ternary solvent system in the presence of KOt-Bu and CaH$_2$.[10] The selection of 13 instead of 4 meant that Montgomery's amination step was no longer required, saving a single synthetic step. The formation of the purine potassium salt and the coupling reaction were carried out in one vessel (Scheme 8). The choice of solvent mixture had a significant influence on the anomeric selectivity and conversion. The additive CaH$_2$ had a beneficial effect by removing trace amounts of water from the solvent. After optimization, intermediate 14 could be obtained from the coupling reaction with a 15:1 β-:α-ratio which was upgraded to an anomeric ratio of 80:1 (β/α) in 50% yield with through crystallization from butyl acetate-heptane and re-slurrying with MeOH. The deprotection of the β-enriched 14 gave crude clofarabine, which after crystallization from MeOH, gave pure clofarabine in 64% yield. The yield from carbohydrate 8 was 32%, and therefore the overall yield was up to about 14% based on starting carbohydrate 9.

Therefore, there is still need for an improved process of making clofarabine.

SUMMARY OF THE INVENTION

The first aspect of the present application is a process comprising:

mixing guanidine carbonate, a fluorinating agent, and a compound of formula VII wherein each R$^4$ is independently a hydroxyl protecting group, OR$^6$ is a leaving group to obtain a compound of formula VIII:

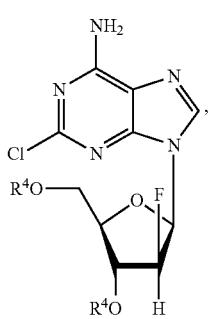

VIII wherein R⁴ is as defined above.

Preferably, the above-described process comprises a step of deprotecting the compound of formula VIII to obtain clofarabine of formula I

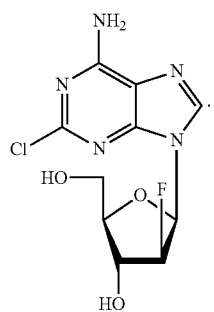

I

The compound of formula VIII used in the deprotecting step preferably comprises no greater than 0.10% (peak area) by HPLC of a compound of formula IX:

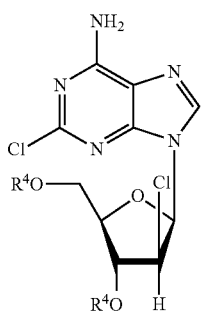

IX wherein R⁴ is as defined above.

The compound of formula VIII to be deprotected preferably has a HPLC purity (peak area %) of at least 99%, more preferably 99.5%, and most preferably 99.8%. The compound of formula VIII to be deprotected preferably contains a no greater than 0.1% by HPLC (peak area) compound of formula J, a no greater than 0.1% by HPLC (peak area) compound of formula X, a no greater than 0.1% by HPLC (peak area) compound of formula Y, and no greater than 0.15% by HPLC (peak area) of the total amount of the compound of formula X and the compound of formula Y:

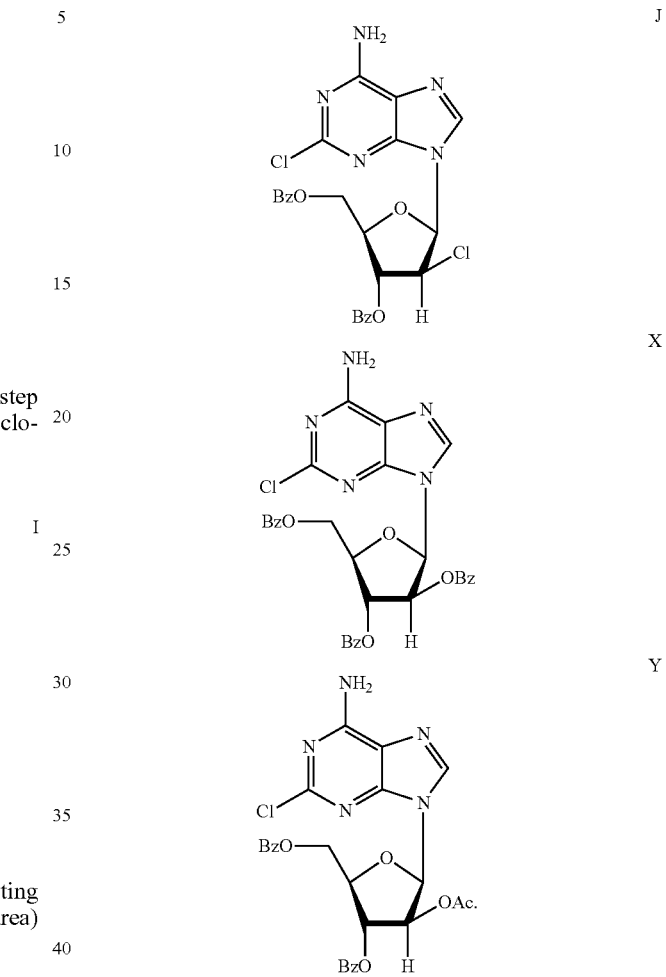

The fluorinating agent is preferably HF or a mixture of HF and an organic Lewis base. The organic Lewis base is preferably an amine. The "mixture" herein refers to any discrete or non-discrete composition, complex, or salt that may be formed from mixing HF and the organic Lewis base. Discrete compositions that can be referred to as complexes include: triethylamine tris(hydrogen fluoride) (3HF.Et₃N), known as TREAT HF, triethylamine bis(hydrogen fluoride) (2HF.Et₃N), and triethylamine hydrogen fluoride (HF.Et₃N). Non-discrete compositions might be formed by combinations of HF and the Lewis base that do not form a single complex, but might be mixtures, or might possess a molar excess of the Lewis base with respect to HF.

A solvent may be added to the mixture of guanidine carbonate, the fluorinating agent, and the compound of formula VII in the above mixing step. The solvent is preferably an ester solvent, more preferably EtOAc or n-PrOAc. The solvent may also be one of the following: PhMe, EtOAc/PhMe, DCE, DCM, Et₃N, THF, i-PrOAc and BuOAc.

The compound of formula VII is preferably prepared by derivatizing a compound of formula (V)

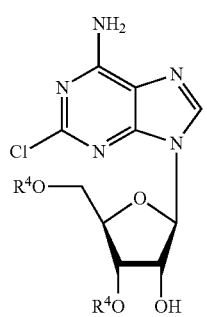

wherein R⁴ is as defined above.

The compound of formula (V) may be prepared by a process comprising:

1) partially deprotecting a compound of formula (IV):

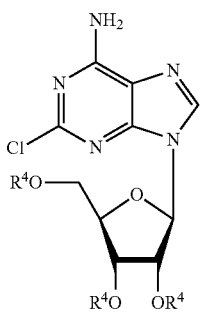

to obtain a first reaction mixture comprising the compound of formula (V) and a compound of formula (VI)

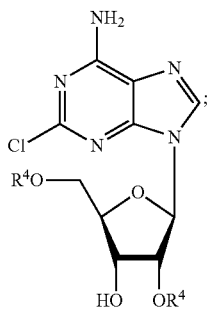

2) isomerizing the compound of formula VI in the mixture obtained in step 1) to the compound of formula V in a solvent at an elevated temperature to obtain a second reaction mixture; and 3) isolating the compound of formula (V) from second reaction mixture.

The partial deprotection of IV is preferably carried out in the presence of a nucleophilic reagent, more preferably hydrazine hydrate in a mixture of glacial AcOH and pyridine or hydroxylaminium acetate in pyridine.

The partial deprotection step using hydrazine hydrate may be conducted in a mixture of pyridine and acetic acid, and after extracting the resulting solution of the mixture (VI) and (V) in an organic solvent (for example MIBK or DCM) with an aqueous base solution (for example aq. NaHCO₃), followed by the isomerisation step and recrystallisation of (V), the amount of residual acetic acid in the compound of formula (V) is preferably controlled to no more than 0.5% weight/weight by GC.

The mixture comprising the compound of formula (V) and formula (VI) obtained in step 1) may be diluted with an organic solvent that is not substantially miscible with water, such as MIBK or DCM, more preferably MIBK, and processed by aqueous work-up comprising an aqueous acid extraction operation and an aqueous base extraction operation to substantially remove hydrazine and hydrazine derivatives (such as BzNHNH₂), pyridine and acetic acid, followed by concentration of the MIBK solution of compounds of formula (V) and formula (VI) which is then diluted with a second solvent, such as MeOH, without any additional purifying step and then directly subjected to isomerizing of step 2).

The compound of formula (IV) is prepared by: coupling a protected ribofuranose of formula III:

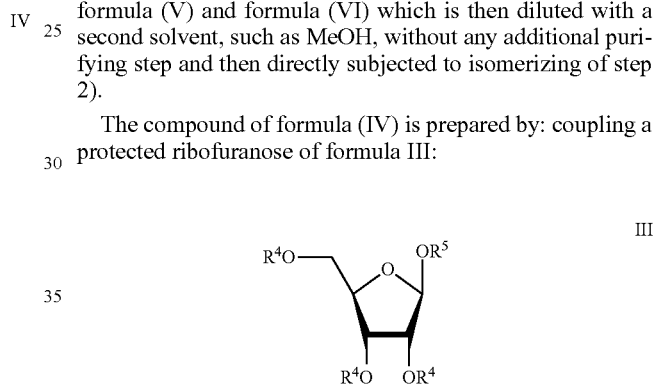

wherein R⁴ is as defined above, OR⁵ is an leaving group, with a silylated 2-chloroadenine of formula II:

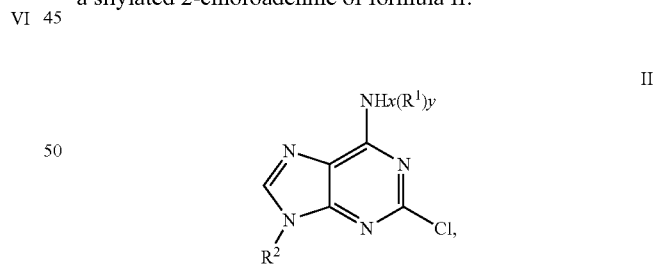

wherein $R^1$ is $Si(R^3)_3$, $R^2$ is hydrogen or $R^1$, $R^3$ is alkyl, alkenyl, alkynyl, aryl or heteroaryl and contains 1 to 10 carbon atoms, and x is 0 or 1 whilst y is 2 or 1, respectively, in the presence of a Lewis acid or a Brønsted acid, such as those derived from sulfonic acids, which include trimethylsilyl triflate (TMSOTf) and triflic acid (TfOH). Preferably, the silylated 2-chloroadenine is not previously isolated.

The silylated 2-chloroadenine of formula (II) may be prepared by: silylating 2-chloroadenine (2-chloro-6-aminopurine) with a silylating agent in an organic solvent or neat (i.e., silylating agent acts as the solvent).

The second aspect of the present application is a process comprising:

1) mixing a solvent and a compound of formula VI

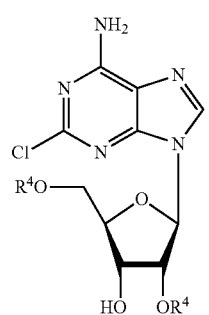

wherein each R⁴ is independently a hydroxy protecting group, to obtain a first mixture;

2) heating the first mixture of step 1) for a sufficient period of time so that a substantial amount of the compound of formula VI is isomerized to a compound of formula (V)

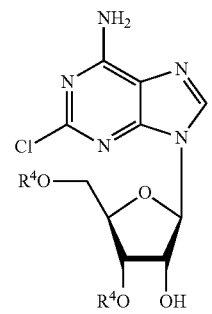

wherein each R⁴ is as defined above, to obtain a second mixture comprising the compound of formula (VI) and the compound of formula (V); and 3) isolating the compound of formula (V) from the second mixture to obtain an isolated compound of formula (V) and a third mixture comprising the compound of formula (VI).

The compound of formula (VI) used in the mixing step may exist as a substantially pure compound or more frequently in a mixture with other compounds, such as compound of formula (V).

The heating step is preferably carried out for at least 5 hours, more preferably at least 6 hours. Depending on the specific conditions of the heating step, such as solvent and temperature, the "sufficient period of time" may be adjusted so that a substantial amount of the compound of formula VI is isomerized to a compound of formula (V). For example, the heating step may be conducted for five to twenty four hours in DMSO or sec-BuOH at 100° C.

Preferably, the isomerisation is conducted substantially in the absence of AcOH, pyridine and hydrazine or hydrazine hydrate, hydroxylaminium acetate or silica gel.

The solvent used in the above process may be selected so that the first mixture is heterogeneous during the heating step. Preferably, the compound of formula (V) is substantially less dissolved in the solvent than the compound of formula (VI) during the heating step, but the compound of formula (V) is sufficiently insoluble, and the compound of formula (VI) is sufficiently soluble in the solvent when the elevated temperature is lowered to effect the isolation of the compound of formula (V) by selective crystallization. For example, the compound of formula (V) has a solubility at 25° C. of preferably less than 10 grams per 1000 gram of solvent, and more preferably less than 1 gram per 1000 grams of solvent.

When the first mixture is heterogeneous during the heating step, the compound of formula (VI) is preferably isomerized to the compound of formula (V) until the level of the compound of formula (VI) in the solution phase of the second mixture reaches a steady state.

On the other hand, the solvent used in the above process may also be selected so that the first mixture is in form of a homogenous solution during the heating step, but the compound of formula (V) is substantially insoluble, and the compound of formula (VI) is substantially soluble in the solvent when the elevated temperature is lowered to effect the isolation of the compound of formula (V) by selective crystallization.

When the first mixture during heating is in form of a homogenous solution, the process in accordance with the present invention preferably comprises repeating at least once the steps 1)-3) to process the third mixture.

The first mixture is preferably heated to a temperature of about 35° C. to 120° C., more preferably, for some solvents, such as MeOH and BuOH, the first mixture is heated to the reflux temperature of the specific solvent used.

The solvent used in the above process for mixing with the compound of formula (VI) is preferably selected from the group consisting of a lower alcohol ($C_1$-$C_6$), DMSO, and combinations thereof.

The isolated compound of formula (V) is preferably recrystallized from at least one solvent such that the amount of residual acetic acid in the recrystallized compound of formula (V) is controlled to no more than 0.5 weight % by GC assay. The at least one solvent is preferably a mixture of DMSO and MeOH.

The compound of formula (V) obtained in accordance with the present application may be converted to clofarabine.

The above described isomerization reaction may be conveniently monitored by measuring the HPLC assay or HPLC purity of compound VI in the homogenous solution of the heated first mixture or the solution phase of the heated heterogeneous first mixture. In that way, one may determine a sufficient period of time for the heating step. For example, when the HPLC purity of compound VI in the homogenous solution of the first mixture or when the HPLC assay of compound VI in the solution phase of the first mixture in heterogeneous form stops decreasing or decreases no more than 0.1% over a 2 hour period, the heating step may be terminated by cooling to room temperature. Alternatively, when the heated first mixture is in heterogeneous form and the assay of compound VI in the solution phase is no more than 0.3% when about 10 to 20 volumes of solvent are used with respect to the weight of non-solvent components of the first mixture ("non-solvent components of the first mixture" refers to the weight of V+VI), the heating step may be terminated. The isomerisation reaction can typically be conducted, within a 6 to 10 hour period and then terminated.

When the heated first mixture is in heterogeneous form it is desirable that most of compound (VI) is isomerized. The isolated compound of formula (V) contains only a low level of compound of formula (VI). Compound (V) may be recovered in filter cake by filtration of the heterogeneous mixture following cooling to room temperature with about 94-96% HPLC purity, contaminated with about 2-4% HPLC purity of compound (VI), and the filtrate itself preferably contains a minimal amount of compound of formula (VI).

When the heated first mixture is a homogeneous solution, a sufficient period of time is preferably the period of time during which the equilibrium of the isomerization is reached. In a homogeneous solution of a mixture of V and VI, the equilibrium is about 2:1 (weight/weight or mole/mole based on HPLC area %).

It is preferable that the first mixture is heated until the isomerization of a compound of formula VI to a compound of formula (V) is complete, substantially complete, or reaches a steady state. When the heated first mixture is in heterogeneous form, one may determine that the isomerization is substantially complete or complete if there is no further or little yield increase of the compound of formula (V) in the solid phase (i.e., which is mostly composed of the compound of formula (V)). When the heated mixture is a homogenous solution, one may determine that the isomerization is complete or substantially complete, when the isomerization equilibrium is achieved, e.g., if the ratio of the compound of formula (VI) and the compound of formula (V) reaches a steady state, which typically about 2:1.

A third aspect of the present application is a process comprising:
1) irradiating a compound of formula VIb in a solid form

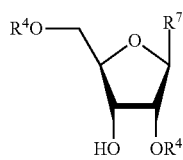

VIb wherein each $R^4$ is independently a hydroxy protecting group and $R^7$ is a heterocyclic radical with electromagnetic radiation so that at least partial amount of the compound of formula VIb is isomerized to a compound of formula (Vb)

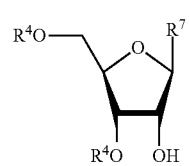

Vb wherein each $R^4$ and $R^7$ are as defined above; and
2) isolating the compound of formula (Vb) from the compound of formula (VIb). The isolating of step 2 can be conducted by separation or purification methods including crystallisation or chromatography or a combination of separation methods. When the compound of formula Vb is V and VIb is VI then the separation method can be crystallisation from a solvent composed of MeOH and DMSO. $R^7$ is a heterocyclic radical such a nucleobase radicals such as but not limited to 2-chloro-adenin-9-yl, adeninyl, uracilyl, guaninyl, cytosinyl and thyminyl.

The electromagnetic radiation is preferably infrared radiation.

Other objects and features of the present invention will become apparent from the following detailed description.

DETAILED DESCRIPTION OF THE PRESENTLY PREFERRED EMBODIMENTS

The following embodiments are provided to further explain, but not to limit, the present invention.

As used herein, the term "hydroxyl protecting group" refers to a group intended to protect a hydroxyl group against undesirable reactions during synthetic procedures. For example, the hydroxyl protecting groups include alkyl, cycloalkyl, arylalkyl, aryl, ethers, esters, cyclic ethers, cyclic esters, cyclic acetal, and cyclic ketal. Preferably, the hydroxyl protecting group in this application is an acyl group, more preferably a benzoyl group or a substituted benzoyl group.

As used herein, the term "leaving group" generally refers to a group that is displaceable by a nucleophile. Leaving groups are known in the art. Examples of leaving groups include, but are not limited to, esters (e.g., acetate, benzoate), halides (e.g., I, Br, F, Cl), sulfonates (e.g., mesylate, tosylate, triflate), sulfides (e.g., $SCH_3$), N-hydroxysuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, hydrazines, hydroxylamines, thiols, alcohols, Grignard reagents, anionic species (e.g., alkoxides, metal amides, carbanions) and the like. In this application, in the leaving group $OR^5$, $R^5$ is preferably an acyl group, such as acetyl. The leaving group $OR^6$ in this application is preferably a sulfonate ester or sulfamate (e.g., $R^6=SO_2$Nhet) where NHet is a nitrogen containing heteroaromatic ring) and contains 1-12 carbon atoms, and $R^6$ is preferably $SO_2C_nF_{2n+1}$. As used herein, the term "thermal isomerization" refers to isomerisation that occurs as a result of heat transfer from a heat source to the isomerizing substance or substances. As used herein, the term "thermal conditions" refers to reaction conditions in which heat transfer from a heat source to the reaction mixture occurs. Unless otherwise stated, values of percentage purity by HPLC are peak area % values.

The present application encompasses a novel synthesis of clofarabine (a.k.a. 2-chloro-9-(2'-deoxy-2'-fluoro-β-D-arabinofuranosyl)-adenine) which involves the direct coupling of 1-O-acetyl-2,3,5-tri-O-benzoyl-ribofuranose (a.k.a. protected carbohydrate C) and bis-silylated 2-chloroadenine (a.k.a. silylated nucleobase B), selective mono-debenzoylation, sulfonate ester formation (sulfonylation), fluorination and finally deprotection (Scheme 1).

Scheme 1 - Synthesis of clofarabine in accordance with an embodiment of this invention

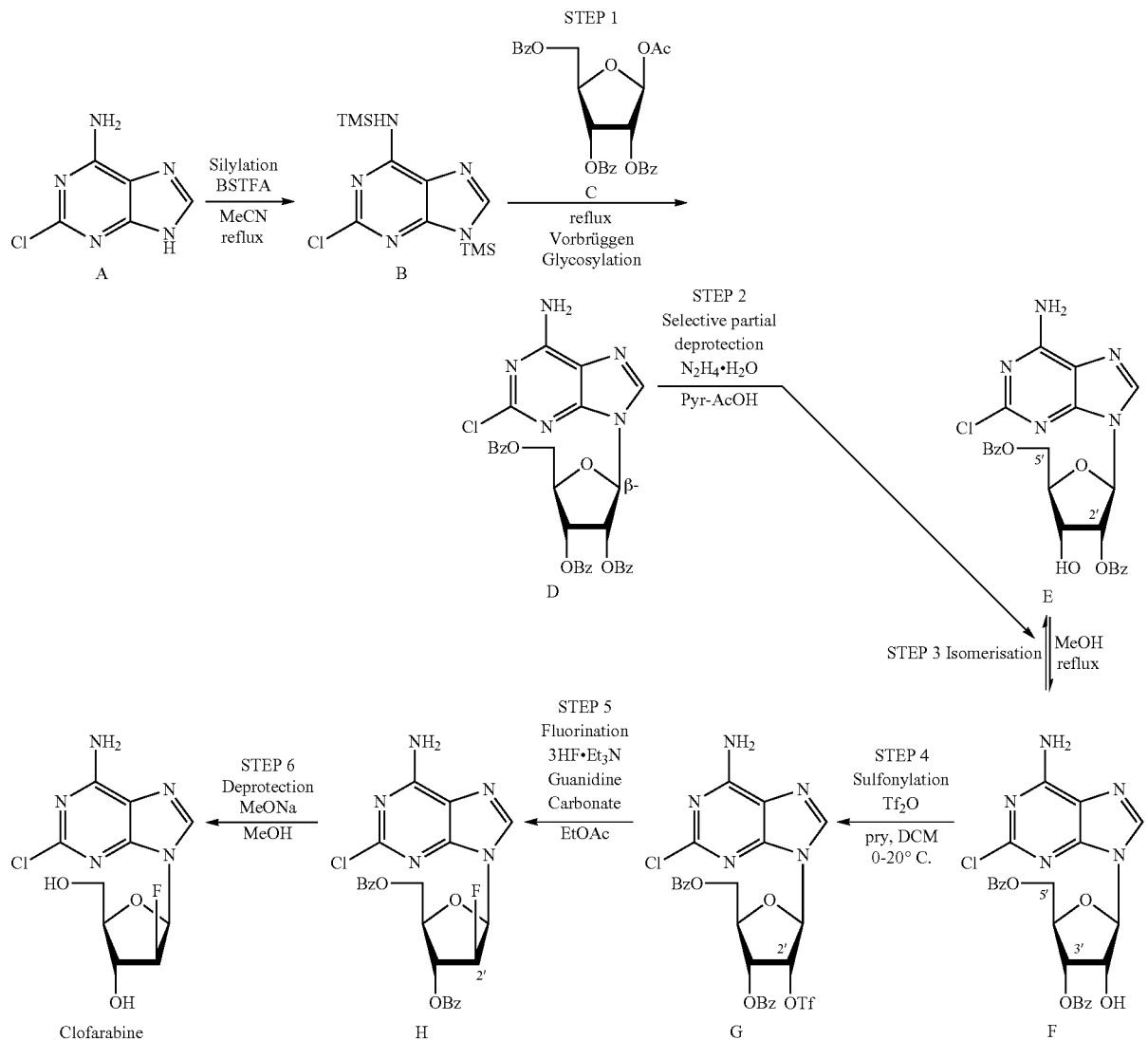

In the first step, the protected carbohydrate C and nucleobase B coupling step gives solely or substantially the desired β-N9 anomer (D). The high selectivity in this Vorbrüggen glycosylation reaction is a result of participation of the C2-OBz group that acts as a strong stereo-directing group.

Following this, partial debenzoylation using excess hydrazine hydrate (i.e., hydrazinolysis; Ishido et al.[11]) in glacial AcOH and pyridine (1:4 v/v) or excess hydroxylaminium acetate (i.e., hydroxyaminolysis; Ishido et al.[12]) in pyridine gives a mixture of the desired 3',5'-di-O-benzoyl isomer F and the unwanted 2',5'-di-O-benzoyl regioisomer E, along with some of the undesired bis-deprotected 5'-O-benzoyl ester. When hydrazine hydrate in glacial AcOH and pyridine was used, an approximately 2:1 ratio of the desired 3',5'-di-O-benzoyl isomer F to the undesired 2',5'-di-O-benzoyl regioisomer E is observed by HPLC analysis of the reaction product mixture, and this approximately 2:1 ratio is maintained after isolation by aqueous work-up without a crystallisation step. The isomers can be separated by fractional crystallisation, however, because the original mixture relatively contains about one third of 2',5'-di-O-benzoyl regioisomer E (relative to F) in the 2',5'-di-O-benzoyl regioisomer E and 3',5'-di-O-benzoyl isomer F mixture, the maximum theoretical yield of the 3',5'-di-O-benzoyl isomer F is about 67%. Therefore, the partial deprotection reaction of compound D results in a significant yield loss results due to the co-formation of the undesired 2',5'-di-O-benzoyl regioisomer E. This is wasteful and therefore there exists a need for recycling of the undesired 2',5'-di-O-benzoyl regioisomer E. An aspect of the invention herein addresses this need.

Isomerisation of 2',5'-di-O-benzoyl-ribonucelosides, prepared by hydrazinolysis[11] or hydroxyaminolysis[12] of fully acylated purine and pyrimidine ribonucleosides to provide a mixture along with 3',5'-di-O-benzoyl-ribonucleosides, has been effected by chromatographic treatment on Wakogel C-300 (this is a commercial variety of silica gel) by Ishido et al.[13] The degree of isomerisation depends on the chemical structure of the nucleobase moiety. Ishido et. al.[14] reported that treatment of 3',5'-di-O-benzoyl-N[6]-benzyladenosine or 2',5'-di-O-benzoyl-N[6]-benzyladenosine with hydroxylaminium acetate in pyridine in separate experiments rapidly (1.5-2 h) isomerized to give 7:3 mixtures, respectively. However, selective isomerisation to provide the 3',5'-di-O-benzoyl-$N^6$-benzyladenosine again required chromatography on Wakogel C-300. For the specific application of the isomerisation of mixtures of E and F on manufacturing scales to efficiently provide substantially or completely pure F devoid of compound E, the inventors did not find the above-mentioned chromatographic isomerisation effective. Surprisingly, however, the inventors discovered that when a mixture of E (21.1% by HPLC) and F (70.8% by HPLC) (typically the E/F mixture is almost exactly 2:1 by HPLC) as a solid, in the absence of substantial amounts of partial deprotection reagent or buffer, was irradiated under an infrared lamp (250 W infrared light lamp with 0.5 KW power rating), placed about 20 cm from the solid that provided an air temperature of about 60° C., a slow relative enrichment of F (78.7% by HPLC) occurred, whilst E (17.2% by HPLC) was seen to decrease, as determined by HPLC analysis (see Table 2). This indicated to the inventors that isomerisation of E to F could proceed under conditions of heat transfer (i.e., when the mixture was heated by conduction or was heated by irradiation) without the need for silica gel. The rate of isomerisation in this experiment was relatively slow. The inventors did not observe the isomerisation during fractional crystallisation of a mixture of E and F wherein the mixture was dissolved by heating in a solvent. Also the inventors did not detect isomerisation of a mixture of E and F during the drying of 95% pure compound F in vacuo at 50° C. for 4 h, then at 60° C. for 4 h, and then at 80° C. for 2 h (Table 11). Thus, useful degrees of isomerisation of E and F require certain reaction conditions that are not encountered during the implementation of typical crystallisation and drying operations.

TABLE 1

| Drying condition in vacuo | HPLC purity compound E | HPLC purity compound F |
|---|---|---|
| Drying at 50° C. for 4 h | 0.36% | 95.2% |
| Continue drying at 60° C. for 4 h | 0.34% | 95.2% |
| Continue drying at 80° C. for 2 h | 0.33% | 95.1% |

The inventors did not observe isomerisation under standard crystallization conditions.

TABLE 2

Isomerisation of a mixture of E and F
as a solid in under an infrared lamp

| Time | Compound (E)$^a$ | Compound (F)$^a$ |
|---|---|---|
| 0 h | 21.1% | 70.8% |
| 2 h | 20.7% | 71.9% |
| 5 h | 18.2% | 73.7% |
| 10.5 h | 17.2% | 78.7% |

$^a$Area percent, as determined by HPLC analysis.

Based on the observation that mixture of E and F isomerized under conditions of heat transfer, the inventors conducted further experiments with the aim of developing a novel and industrially useful method of isomerizing mixtures of E and F utilizing heat transfer. The inventors unexpectedly discovered that a mixture of compounds of the formula F and E underwent isomerisation when dissolved in a heated solvent (i.e., as a homogenous solution) when heated at temperatures above room temperature for a period of time. In 10 volumes of DMSO at about 100° C., a 21:1 mixture of F and E isomerized to provide a 1.9:1 mixture at between 6.5 h and 19 h (the ratio was 3.3:1 at 6.5 h with no significant change (from 98.4 area % to 98.7 area %) in the total combined area % of F and E). In 20 volumes of sec-BuOH at about 100° C., a 23:1 mixture of F (90% HPLC purity) and E isomerized to provide a 1.9:1 mixture (63.3% compound F and 33.8% compound E by HPLC analysis of the mixture) at between 5 h and 23.5 h (the ratio was 2.1:1 at 5 h with only 1% change (from 94 area % to 93 area %) in the total combined area % of F and E). An approximately 2:1 ratio of F and E was consistently formed under the homogenous conditions. When the reaction solution that had provided a 1.9:1 mixture of F and E described above in 20 volumes of sec-BuOH at about 100° C. was cooled to about 10° C., compound F crystallised with 97% HPLC purity (only 2% compound E) in about 60% yield based on the original 23:1 mixture of F and E, which is consistent with efficient recover of the compound F from the 1.9:1 mixture of F and E. Compound E was found in about 82% HPLC purity (and 15% compound F) in the mother liquors of the crystallisation, in about 40% yield. When the mother liquors from an equivalent experiment (but which had be initiated utilising a 1.4:1 mixture of F and E before the first equilibration and crystallisation) containing the enriched compound E was heated again at about 100° C. for 12 hours, it re-equilibrated and a 1.9:1 ratio of F and E was formed which after cooling to room temperature provided crystals of compound F crystallised with 96% HPLC purity (only 2% compound E) in about 17% yield based on the original mixture of F and E. Thus, by re-equilibration (i.e., isomerisation until the static point (equilibrium), as can be determined by HPLC analysis of the solution, is obtained) of the crystallisation mother liquors that are enriched with the undesired compound E, a greater than theoretical yield of compound F, could be obtained. These experiments confirmed that heat transfer (i.e., heating) could be used to promote the isomerisation and therefore recycle of the undesired isomer E to provide greater amounts of isomer F beyond the amounts that the partial debenzoylation step of ribonucleoside D can provide. A disadvantage of this protocol is that the mother liquors must be isolated and further equilibrated and then crystallised again. Therefore the inventors still saw a need for an improved process, and reasoned that if a solvent or mixture of solvents could be identified in which compound F was substantially insoluble but in which compound E was substantially soluble at temperatures at which the thermal isomerisation of compound E to F could occur, a greater than theoretical yield of compound F should be generated in the solid phase and the compound E should be substantially or fully converted to compound F, assuming that the heating was conducted for long enough time.

In line with this need the inventors discovered that the undesired 2',5'-di-O-benzoyl regioisomer E can be isomerized to the desired 3',5'-di-O-benzoyl isomer F under thermal conditions in a solvent by the careful selection reaction parameters (namely, solvent, concentration and temperature) such that the desired 3',5'-di-O-benzoyl isomer F is located substantially in the solid phase whilst at the same time the undesired isomer is located in the liquid phase. Under such conditions, the combined phenomena of equilibration of the two isomers E and F in the solution phase and the continual precipitation of newly formed 3',5'-di-O-benzoyl isomer F forces the reaction mixture (i.e., the solid plus solution phases) towards a total higher 3',5'-di-O-benzoyl isomer F content than was started with. That is, a greater than 100% theoretical recovery yield of isomer F can be obtained. The preferred solvent for this conversion was MeOH. The preferred temperature at atmospheric pressure was the reflux temperature of MeOH (i.e., about 65° C.). For example a 1.0 g heterogeneous mixture of 2-chloro-9-(2',5'-di-O-benzoyl-β-D-ribofuranosyl)-adenine (E) (27.4% purity by HPLC) and 2-chloro-9-(3',5'-di-O-benzoyl-β-D-ribofuranosyl)-adenine (F) (47.0% purity by HPLC) was isomerized in MeOH (20 mL) at reflux temperature (about 65° C.) for 66 hours, after cooling to room temperature, filtration and drying, 0.62 g of 96.6% pure 2-chloro-9-(3',5'-di-O-benzoyl-β-D-ribofuranosyl)-adenine (F) was obtained which is equivalent to a 126% yield calculated based on compound F, or an 80% yield calculated based on the mixture of compounds E and F in the original mixture. The filtrate contained very little of compound E and F (1.6% HPLC purity compound F and 5.8% HPLC purity compound E). On a larger scale, this method was convenient, fast and efficient. The isomerisation reaction can be conveniently monitored by measuring the HPLC assay of compound E in the solution phase of the heterogeneous mixture. When the HPLC assay of compound E in the solution phase stops decreasing, or does not decrease by more than 0.1% over a 2 hour period, or the assay of compound E in the solution phase is no more than 0.3%, the reaction can be terminated by cooling to room temperature. The isomerisation reaction can typically be conducted within a 6 to 10 hour period and then terminated. Following this isomerization, the desired 3',5'-di-O-benzoyl isomer F is conveniently isolated by filtration. In this way, compound (F) can be recovered in the filter cake with about 94-96% HPLC purity, contaminated with about 2-4% HPLC purity of compound (E).

Bauman and Wirsching[15] disclosed a method for the isolation of 3',5'-di-O-acetyl-2-fluoroadenosine from a mixture of including 3',5'-di-O-acetyl-2-fluoroadenosine and 2',5'-di-O-acetyl-2-fluoroadenosine that involves fractional crystallisation from MeCN or MeCN/acetone, but no isomerisation method is taught.

In the next step, the 3',5'-di-O-benzoyl isomer F is sulfonylated at C2'-OH using a sulfonylation agent (viz. the sulfonic anhydride Tf$_2$O). It is possible that other leaving groups, such heteroaromatic sulfonate (e.g., imidazolesulfonate), could be used in place of triflate to activate the C2'-OH.

A fluorination reagent is then used to substitute the sulfonate group at C2' in the presence of a base or base salt (such as guanidine carbonate). The fluorination reagent 3HF.Et$_3$N is preferred as it is non-corrosive[16] and it is applicable to large scale synthesis. Because commercial supplies of 3HF.Et$_3$N contain chloride (probably in the form of HCl), and because the chloride ion is more reactive than the fluoride ion under the reaction conditions tested herein, significant amounts of the undesired chloride compound J, which is an analogue of the desired penultimate precursor H, are formed (Scheme 9). Because the deprotected form (i.e., compound K) of chloride compound J can be very difficult to remove from the API its levels need to be limited in the upstream synthetic process. The inventors surprisingly discovered that this control can be achieved by the use of 3HF.Et$_3$N in combination with guanidine carbonate. When guanidine carbonate was used as an additive in the fluorination reaction, relatively lower and acceptable amounts of the chloride analogue J were formed. Following fluorination, the resultant protected clofarabine H was subjected to crystallization to remove impurities that would otherwise affect the quality of the final API product.

In the final synthetic step, the purified protected clofarabine H is deprotected to give very pure clofarabine without detectable amounts of isomers. This can be further crystalized as a routine matter to ensure the API meets its specification.

One significant issue and source of inefficiency with the synthetic methods of the prior art clofarabine syntheses that utilize the coupling of protected 2-deoxy-2-fluoro-arabinofuranosides with purine nucleobases, is the concomitant formation of regio- and stereoisomers including α-N9, α-N7 and β-N7 (Figure 1) in addition to the desired β-N9 isomer. The α-N9 isomer is a particularly common undesired impurity (see Scheme 4, 6, 7 and 8 for examples of syntheses in which this stereoisomer is formed) and is difficult to remove, requiring either chromatography or crystallization to remove it.

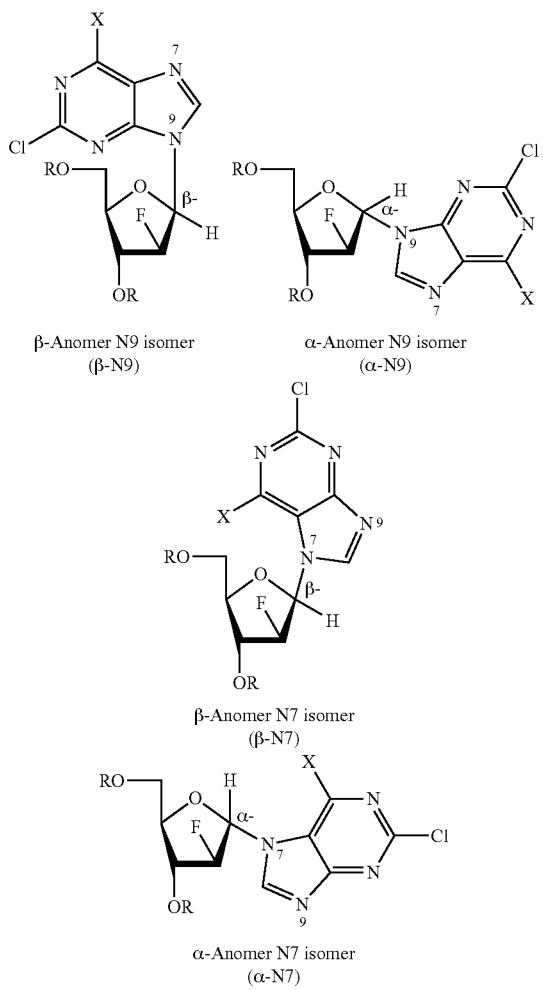

FIG. 1 - Isomers of 2-deoxy-2-fluoro-arabinofuranosides coupled with purine nucleobases β-Anomer N9 isomer (β-N9)

α-Anomer N9 isomer (α-N9)

β-Anomer N7 isomer (β-N7)

α-Anomer N7 isomer (α-N7)

X = Cl or NH$_2$

By contrast, in accordance with an embodiment of this invention, the protected β-N9 isomer, protected 2-chloroadenosine D, is obtained selectively and completely, or substantially, free of the α-N9 isomer D2, the β-N7 isomer D3 and α-N7 isomer D4 (Figure 2) meaning that the downstream synthetic intermediates are also completely or substantially free of isomers. This is achieved by conducting the nucleoside coupling reaction on a ribose carbohydrate system in which the C2' oxygen is present, in contrast to a 2'-deoxy-ribose system in which the C2'-oxygen is absent. That is, in this invention the protected D-ribofuranose C (9) is coupled with the bis-silylated 2-chloroadenine B. Without being bound by theory, the undesired α-N9 isomer is not formed in appreciable amounts due to neighboring group participation (also known as anchimeric assistance) of the C2-OBz group (Scheme 1) that direct the nucleobase to the n-face of the carbohydrate ring during coupling of the two units. Furthermore, the coupling step reaction conditions might allow reversibility of the nucleoside formation meaning that isomerization of the undesired N7 regioisomers D3 and D4 to the desired β-N9 isomer D can occur.

One embodiment of this invention is the synthesis of clofarabine in which the nucleoside is constructed by the coupling of the nucleobase and carbohydrate units before the C2' fluorine atom is installed in the carbohydrate ring.

FIG. 2 - Isomers of ribofuranoside coupled with silylated 2-chloroadenine

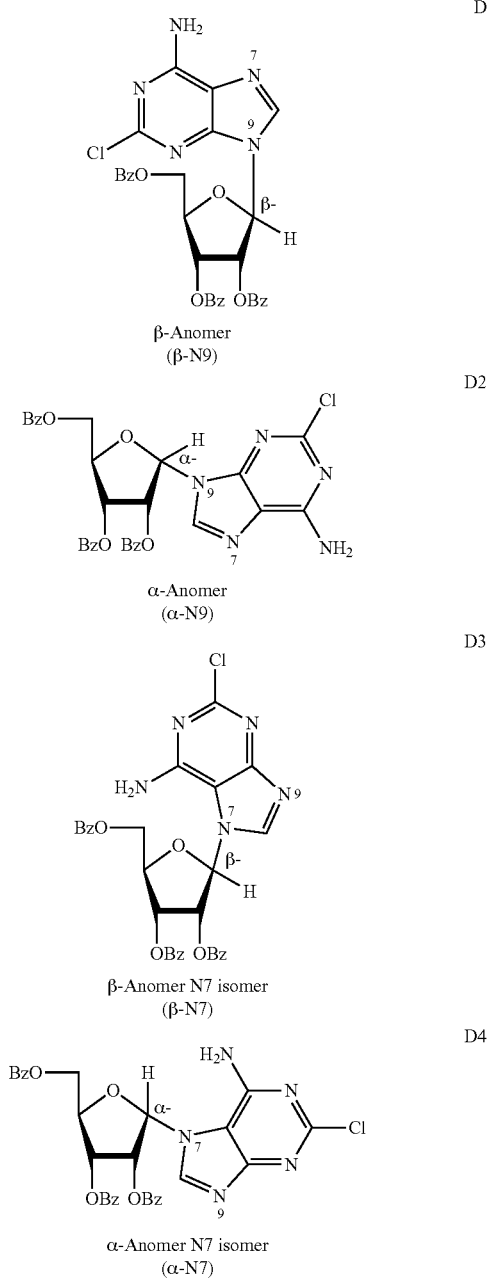

The protected 2-chloroadenosine D is regioselectively mono-deprotected using hydrazine hydrate in pyridine and acetic acid or hydroxylaminium acetate in pyridine following similar methods of Ishido[11,12] to give a mixture of the desired 3',5'-di-O-benzoyl nucleoside F and the unwanted 2',5'-di-O-benzoyl regioisomer E, along with some of the undesired bis-deprotected 5'-O-benzoyl nucleoside (5'-O-benzoyl-2-chloroadenosine). In one aspect of this step, the crude reaction product is washed with an aqueous base, preferably NaHCO₃ until the GC assay of AcOH in the organic phase is <=0.5% by weight. This is important to ensure that the API can be produced free of isomers such as 2-chloro-9-(β-D-arabinofuranosyl)-adenine. Although this mixture comprises a relatively moderate yield of the desired 3',5'-di-O-benzoyl isomer F due to the co-formation of the unwanted 2',5'-di-O-benzoyl regioisomer E, the inventors discovered that heating the mixture in solvents including alcohols, preferably MeOH, increase the absolute amount of 3',5'-di-O-benzoyl isomer F in the mixture when it is only partially soluble. Without being bound by theory, this is due to an equilibrium driven isomerisation reaction that proceeds by means of acyl migration between the C2'-O and C3'-O positions, which enriches F because the desired 3',5'-di-O-benzoyl isomer F is situated substantially in the solid phase of the mixture whilst at the same time the undesired regioisomer 2',5'-di-O-benzoyl isomer E is located substantially in the liquid phase. It was reported in the literature by Ishido et al.[14] that some partially protected ribonucleosides undergo isomerisation during chromatography on silica gel. The inventors of the invention herein did not find that this was effective for the isomerization of compound E and F because it was not considered practical or efficient for implementation on an industrial scale. Other methods disclosed[15] for separation of 3',5'-di-O-acyl and 2',5'-di-O-acyl isomers rely on fractional crystallisation or chromatography.

In the solution phase of the reaction mixture the equilibrium between the regioisomers E and F in conjunction with the simultaneous precipitation of newly formed 3',5'-di-O-benzoyl isomer F pushes the total composition of the reaction mixture (said plus solution phases) towards one comprising a higher amount of 3',5'-di-O-benzoyl isomer F than was started with. Thus, although the equilibrium constant under the reaction conditions in the solution phase provides an approximately 2:1 ratio of the 3',5'-di-O-benzoyl isomer F and 2',5'-di-O-benzoyl isomer E, the desired 3',5'-di-O-benzoyl isomer F is physically removed from the equilibrating mixture by its precipitation (i.e., is transported into the solid phase). The point in time at which the isomerization reaction should be terminated can be determined by periodically measuring the assay of the solution phase and determining when the absolute amount of isomer E in the solution stops decreasing. This isomerisation process is not a fractional crystallisation process because the undesired 2',5'-isomer E is actually consumed (La, by its conversion to isomer F) during the isomerisation reaction, and is not enriched in the solution phase during the reaction. In fact the isomerisation reaction is monitored by consumption of the undesired 2',5'-isomer E in the solution phase during the reaction.

Following the thermal isomerization operation, the requisite 3',5'-di-O-benzoyl isomer F can be obtained substantially free of the 2',5'-di-O-benzoyl isomer E by filtration in an acceptable yield and with a HPLC purity of >95%. Optionally the 3',5'-di-O-benzoyl isomer F can be recrystallized from a solvent system, including from a sulfoxide and alcohol mixture, preferably from MeOH and DMSO. This crystallisation operation, however, is performed to specifically remove hydrazine, other impurities derived from hydrazine (including N-benzoyl hydrazine), and acetic acid from the intermediate, and is not necessary for the purpose of removing stereo- or regioisomers of 3',5'-di-O-benzoyl isomer F since it is already of acceptably enriched. The removal of hydrazine, other impurities derived from hydrazine, and acetic acid from the 3',5'-di-O-benzoyl isomer F is preferred because it ensures that an acceptable purity of clofarabine can be obtained with respect to the International Conference on Harmonisation (ICH) guidelines on impurities in new drug substances (Q3A(R[2])) and the EMEA's (CHMP) Guideline on the Limits of Genotoxic Impurities (2006). After this recrystallization, regioisomer E was typically less than 0.1% by HPLC. By a combination of i) aqueous NaHCO$_3$ extraction of the organic phase during aqueous work-up that is conducted after the partial isomerisation reaction, and ii) recrystallisation of compound F, acetic acid is preferably controlled to <=0.5 weight % by GC assay.

Thus, another embodiment of this invention is the thermal isomerization of the unwanted regioisomer 2',5'-di-O-benzoyl isomer E in MeOH to provide 3',5'-di-O-benzoyl isomer F. Another aspect of this invention in this embodiment is the control of the isomerization reaction by analytical means to obtain the maximum amount of isomer F, and then the isolation of substantially enriched (typically 94-96% by HPLC) isomer F by filtration of the isomerization reaction mixture and finally a subsequent recrystallization of the compound F to obtain compound F free of impurities that could otherwise lead to API of unacceptable purity.

Sulfonylation of C2'-OH of compound F with triflic anhydride (Tf$_2$O) provides 2'-O-trifyl-2-chloroadenosine (G). In one aspect of the invention the crude compound G solution is dried such that the residual level of water is low, preferably less than 1000 ppm as determined by Karl Fischer titration analysis, because this reduces the amount of impurity formation in the next reaction step, which in turn ensures that the purity of the API is achieved specifically with an acceptable level of the stereoisomer 2-chloro-9-(β-D-arabinofuranosyl)-adenine. The inventors discovered that the fluorination of triflate G could be achieved to provide fluoride H in varying yields and purities with KF in the presence of 18-crown-6, KHF$_2$, CsF, TBAF, or 3HF.Et$_3$N reagent in conjunction with amine bases such as Et$_3$N, pyridine, DIPEA, N-methylimidazole, DBU, or guanidine, or in conjunction with amine salts including guanidine carbonate (see Table 3). However, superior results were observed with 3HF.Et$_3$N reagent, preferably when used in conjunction with amine bases or amine salts. 3HF.Et$_3$N is preferred for industrial manufacture because it does not appreciably corrode glass.[16] Because commercial supplies of 3HF.Et$_3$N can contain varying levels of chloride depending on the grade and supplier, and because the chloride ion is more reactive than the fluoride ion under the reaction conditions used for the conversion of compound G to compound H, significant amounts of the undesired chloride J (i.e., the chloride analogue of compound H) are formed (Scheme 9) even when the level of chloride in the fluorination reagent is low.

The inventors discovered, however, that when 3HF.Et$_3$N was used in conjunction with guanidine carbonate that the level of chlorosugar J could be controlled at levels lower than or equal to about 0.3% (peak area % in HPLC trace) in crude H and levels lower than or equal to about 0.10% (by HPLC) in recrystallised H, meaning that after deprotection of protected clofarabine, chlorosugar K was seen at levels lower than or equal to 0.10% (by HPLC) in the API itself. This proved crucial to obtain clofarabine API with purity that was acceptable with respect to the International Conference on Harmonisation (ICH) guidelines on impurities in new drug substances (Q3A(R2)).

Guanidine carbonate provided better results than the free bases that were tested including guanidine free base. Without being bound by theory, this might be a result of the acid and base combination or a phenomenon relating to the pH in the reaction system or altering the nature of the HF-base complex nucleophilicity. Therefore, it is possible that other bases or base salts used in combination with 3HF.Et$_3$N in different or similar amounts, in the same or different solvent systems, might provide similar, equal or better results.

The chlorosugar impurity J that can form in the fluorination step and its subsequent deprotection product K (2'-chloro-clofarabine) proved very difficult to remove from the desired fluoro analogues (i.e., compound H and clofarabine, respectively) by purification, especially clofarabine. In fact, the inventors discovered that under a range of crystallization conditions that chloro impurity K was slightly enriched upon crystallization of clofarabine. Recrystallization of the penultimate precursor H that was contaminated with chlorosugar impurity J from solvent systems including alcohol and ester solvent mixtures, preferably MeOH and EtOAc, led to an enrichment in H with respect to chlorosugar impurity J but the total purity of the chloro impurity J was still too high (meaning that its deprotected analogue K would contaminate clofarabine in unacceptably high levels) if not controlled in the fluorination step by the appropriate choice of fluorination reagent and conditions. Thus, the use of guanidine carbonate as an additive to the fluorination reaction was very important to allow the synthesis of high quality clofarabine API.

TABLE 3

Fluorination of compound G with fluorinating agents to prepare compound H

| Entry | Fluorination agent | Base additive(s) | Solvent, Temperature, Time | Ratio of H to J in isolated solid (ratio in solution) | HPLC area % of J in reaction solution (HPLC area % of J in crude H) | Isolated yield {HPLC area % of J in recrystallised H} |
|---|---|---|---|---|---|---|
| 1 | 3 eq. KF | NA | DCM, 23° C., 12 h | No reaction | — | — |
| 2 | 3 eq. KF/3 eq. 18-crown-6 | NA | EtOAc, 80° C., 3 h | (5.6:1) | 2.5% | — |

TABLE 3-continued

Fluorination of compound G with fluorinating agents to prepare compound H

| Entry | Fluorination agent | Base additive(s) | Solvent, Temperature, Time | Ratio of H to J in isolated solid (ratio in solution) | HPLC area % of J in reaction solution (HPLC area % of J in crude H) | Isolated yield {HPLC area % of J in recrystallised H} |
|---|---|---|---|---|---|---|
| 3 | 3 eq. KHF$_2$ | NA | DMSO, 50° C., 4 h | (0.91:1) | 4.4% | — |
| 4 | 3 eq. CsF | NA | MeCN, 22° C., 4 h | (10:1) | 0.1% | — |
| 5 | 6 eq. CsF | NA | NMP, 100° C., 5 h | Low conversion | — | — |
| 6 | 6 eq. TBAF | NA | MeCN, 23° C., 7 h | (6.7:1) | 0.9% | — |
| 7 | 6 eq. TBAF | NA | MeCN, −15° C., 7 h | (8:1) | 0.5% | — |
| 8 | 6 eq. 3HF•Et$_3$N | 4 eq. Pyridine | EtOAc, 80° C., 23 h | (3.9:1) | 7.6% | — |
| 9 | 6 eq. 3HF•Et$_3$N | 4 eq. DIPEA | EtOAc, 80° C., 3.5 h | 123:1 (139:1) | 0.47% | 59% |
| 10 | 6 eq. 3HF•Et$_3$N | 4 eq. N-Methylimidazole | EtOAc, 80° C., 7 h | 111:1 (108:1) | 0.60% | 54% |
| 11 | 6 eq. 3HF•Et$_3$N | 4 eq. DBU | EtOAc, 80° C., 4.5 h | 137:1 (140:1) | 0.37% | 49% |
| 12 | 3 eq. 3HF•Et$_3$N | 4 eq. Et$_3$N | EtOAc, 80° C., 7 h | 100:1 (103:1) | 0.60% | 61% |
| 13 | 6 eq. 3HF•Et$_3$N | 4 eq. Et$_3$N | EtOAc, 80° C., 4.5 h | 114:1 (94:1) | 0.70% | 58% |
| 14 | 6 eq. 3HF•Et$_3$N | 6 eq. guanidine | EtOAc, 80° C., 4.5 h | 61:1 (62:1) | 0.73% | 47% |
| 15 | 6 eq. 3HF•Et$_3$N | 4 eq. guanidine | EtOAc, 80° C., 6 h | (115:1) | 0.40% | — |
| 16 | 6 eq. 3HF•Et$_3$N | 4 eq. Guanidine carbonate | EtOAc, 80° C., 12 h | 215:1 (235:1) | 0.28% | 50% |
| 17 | 6 eq. 3HF•Et$_3$N | 2 eq. guanidine carbonate 3 eq. Et$_3$N | EtOAc, 80° C., 4.5 h | 580:1 | (0.14%) | 51% |
| 18 | 9 eq. 3HF•Et$_3$N | 4 eq. guanidine carbonate 3 eq. Et$_3$N | EtOAc, 80° C., 10 h | 455:1 | (0.16%) | 57% |
| 19 | 6 eq. 3HF•Et$_3$N | 4 eq. guanidine carbonate 2.0 eq. Et$_3$N | EtOAc, 80° C., 12 h | 684:1 | (0.11%) | 56% {0.07%} |
| 20 | 6 eq. 3HF•Et$_3$N | 4.0 eq. guanidine carbonate | EtOAc, 80° C., 12 h | 919:1 | (0.08%) | 60% {0.07%} |

Thus, another embodiment of this invention is the use of 3HF.Et$_3$N in conjunction with an amine base or amine salt additive, or both, preferably guanidine carbonate and an amine base such as Et$_3$N, and most preferably guanidine carbonate, for the fluorination of triflate G to provide fluoride H. This provides a high HPLC ratio of the fluoride H to chloro impurity J in the non-recrystallized, isolated solid (referred to as crude H), preferably >200:1, more preferably >500:1, most preferably >900:1, as well as a low total HPLC purity of chloro impurity J in crude H (i.e., non-recrystallised) preferably less than or equal to about 0.3 area % by HPLC as seen in Table 2. Another aspect of this embodiment is that compound H is crystallized to provide compound H that conforms to a specific purity specification of HPLC purity preferably >99.0%, more preferably >99.5% and most preferably >99.8% with compounds J, X and Y each individually at <=0.1% HPLC purity. This ensures that clofarabine can be obtained in acceptable purity.

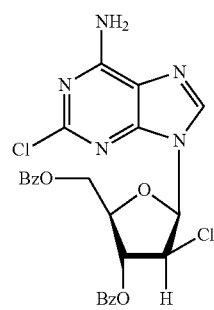

J

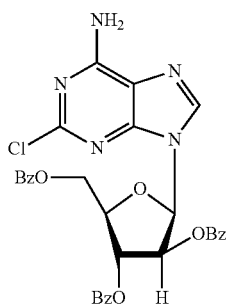

X

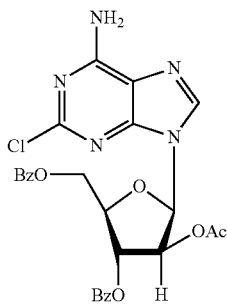

Y

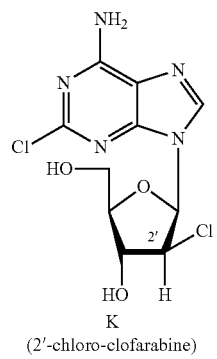

K
(2'-chloro-clofarabine)

The synthesis of clofarabine by use of this invention proceeds in the same number of steps as the competing prior art (counting A (a.k.a. 13) as the starting material) routes and the overall yield from starting carbohydrate C (a.k.a., 9), including recrystallization to furnish API grade material fit for human consumption, is about 15%. In terms of overall yield, the process of this invention is competitive with the prior art methods. In terms of API quality, the embodiment of this invention allows high quality clofarabine to be manufactured by design of the synthetic route and purification operations (e.g., extractions and crystallisations) to control impurities.

Scheme 9

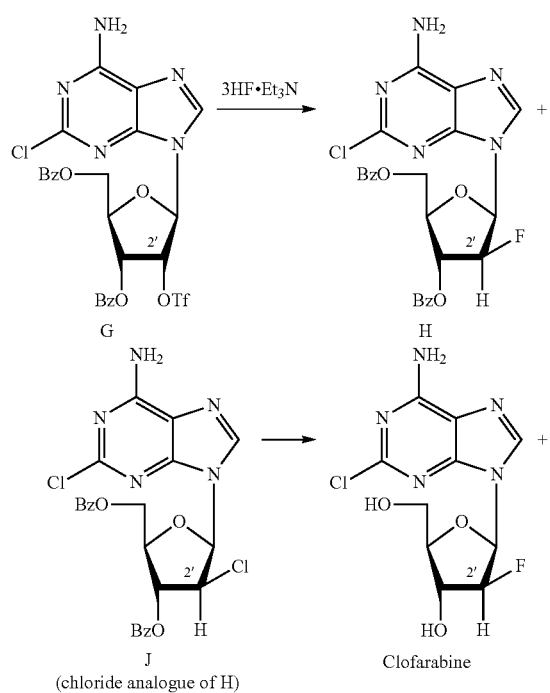

In comparison with the prior art, the embodiments in accordance with the present invention have the following advantages:

1. The present application provides a novel approach to the synthesis of clofarabine. Typically, in previously reported syntheses of clofarabine, the C2' fluorine atom substituent is pre-installed in the carbohydrate ring before the carbohydrate ring is fused with the nucleobase. By contrast, in accordance with an embodiment of the present invention, the fluorine substituent is installed subsequent to the carbohydrate and nucleobase fusion. This means that the undesired stereoisomer α-N9 is not substantially formed.

2. Unlike the majority of previously reported syntheses of clofarabine, the process in accordance with an embodiment of this invention does not require chromatography. This is important because chromatography is typically time consuming and typically utilises relatively large volumes of solvents, which result in a more costly and less environmentally friendly process. For cost, environmental and regulator reasons the spent chromatography solvents must be recovered or disposed of which can be costly. The lack of the need for chromatography as a method of purification in accordance with an embodiment of this invention is in part achieved by fusing the adenine ring to the carbohydrate unit prior to installing the fluorine substituent at C2', which due to the directing effect of the C2-O-ester group in the carbohydrate unit allows very good stereochemical control and thus very good stereochemical purity of the product.

3. Conversion of the unwanted 2',5'-di-O-benzoyl regioisomer (E) into the desired 3',5'-di-O-benzoyl isomer (F) by an analytically controlled heterogeneous (a mixture comprising a solid phase and a liquid phase) thermal isomerization, thereby increasing the overall yield of the desired 3',5'-di-O-benzoyl isomer (F) greater than that produced in the original reaction that it was formed in. This makes the overall process more efficient. By analytical control of this thermal isomerisation the highest yield can be obtained based on the mixture of compounds E and F.

4. The present application discloses a novel modification of fluorination conditions that reduce the amount of highly undesired chloride analogue (J) of protected clofarabine H by specific use of guanidine carbonate additive. This results in increased process efficiency by reducing the burden on the subsequent purification steps.

5. In accordance with an embodiment of this invention, high quality clofarabine API is obtained by controlling the impurity profile of the precursors E and H, and the total HPLC purity of precursor H. Control of the quality of these precursors ensures that high quality API can be obtained that meets the required specification. The purity of clofarabine itself is difficult to upgrade when it is contaminated with several

EXAMPLES

Example 1

Preparation of 2',3',5'-tri-O-benzoyl-2-chloroadenosine (D)

Under an atmosphere of $N_{2(g)}$, 2-chloroadenine (A (9), 50 g, 294.9 mmol), MeCN (600 mL), and BSTFA (227.5 g, 883.8 mmol) were stirred and heated under reflux until the mixture turned mostly clear (about 1 h). TfOH (8.77 g, 58.5 mmol) and 1-O-acetyl-2,3,5-tri-O-benzoyl-β-D-ribofuranose (C, 142.5 g, 282.5 mmol) were sequentially added into the mixture and were stirred at reflux for about 1 h. The mixture was cooled to 20-35° C. and diluted with MTBE (500 mL), and washed over a 0.5 to 1 h period with saturated $NaHCO_3$ (750 mL). The organic phase was evaporated in vacuo at 40 to 50° C. to give 2',3',5'-tri-O-benzoyl-2-chloroadenosine (D): $^1H$ NMR (300 MHz, $CDCl_3$) δ 7.9-8.1 (m, 6H), 7.94 (s, 1H), 7.3-7.6 (m, 9H), 6.45 (d, J=2.7 Hz 1H), 6.15 (m, 2H), 5.30 (s, 2H), 4.90 (dd, $J_{4',5a}$=3.2 Hz, $J_{5'a,5'b}$=12.0 Hz, 1H), 4.82 (m, 1H), 4.72 (dd, $J_{4',5a}$=4.1 Hz, $J_{5'a,5'b}$=12.0 Hz, 1H); $^{13}C$ NMR (75 MHz, $CDCl_3$) δ 166.3, 165.5, 165.4, 156.4, 154.7, 151.1, 139.1, 134.1, 134.1, 133.8, 130.2, 130.1, 129.9, 129.4, 129.0, 128.8, 128.5, 119.1, 86.5, 81.3, 74.6, 71.7, 64.0.

Example 2

Preparation of 2-chloro-9-(3',5'-di-O-benzoyl-β-D-ribofuranosyl)-adenine (F)

To 2',3',5'-tri-O-benzoyl-2-chloroadenosine (D) prepared above was charged AcOH (277 g), pyridine (1109.6 g) and 80% hydrazine hydrate (73.8 g, 1.18 mol) at room temperature The mixture was heated to 75 to 80° C. under an atmosphere of $N_{2(g)}$ until the HPLC purity of compound F stopped increasing within a 2 h period (usually required between 6 to 10 h). The mixture was cooled to 35° C. and diluted with MIBK (3774.4 g) and was then washed at <35° C. with 2 $NH_2SO_4$ (3378 mL) to remove hydrazine and pyridine. The organic phase was washed with saturated $NaHCO_3$ (1734 mL) Until the amount of AcOH in the organic solution phase was not more than 0.5 weight %, as determined by GC assay. The organic phase was evaporated in vacuo at 65° C. until no more distillate was collected to give an approximately 2:1 mixture of 2-chloro-9-(3',5'-di-O-benzoyl-$-D-ribofuranosyl)-adenine (F) and 2-chloro-9-(2',5'-di-O-benzoyl-β-D-ribofuranosyl)-adenine (E) that contained some residual MIBK (typically approximately 2 volumes).

Example 3a

Enrichment of 2-chloro-9-(3',5'-di-O-benzoyl-β-D-ribofuranosyl)-adenine (F) from a mixture of 2-chloro-9-(2',5'-di-O-benzoyl-β-D-ribofuranosyl)-adenine (E) and 2-chloro-9-(3',5'-di-O-benzoyl-β-D-ribofuranosyl)-adenine (F)

MeOH (356.4 g) was charged into the mixture of 2-chloro-9-(2',5'-di-O-benzoyl-β-D-ribofuranosyl)-adenine (E) and 2-chloro-9-(3',5'-di-O-benzoyl-β-D-ribofuranosyl)-adenine (F) prepared above and the resulting heterogeneous mixture was stirred at about 65° C. until the amount of E in the solution phase, as determined by assay, did not significantly decrease within a 2 h period (this took about 10 hours). The heterogeneous mixture was cooled to between 20 to 25° C. and was filtered and the filter cake was washed twice with MeOH (11.09 g each) and dried in vacuo at 50-60° C. for between about 8 h. Using this protocol, the isolated solid 2-chloro-9-(3',5'-di-O-benzoyl-β-D-ribofuranosyl)-adenine (F) was about typically about 94-96% HPLC pure and 2-chloro-9-(2',5'-di-O-benzoyl-β-D-ribofuranosyl)-adenine (E) was about 2-4% HPLC pure.

Example 3b

Enrichment of 2-chloro-9-(3',5'-di-O-benzoyl-β-D-ribofuranosyl)-adenine (F) from a mixture of 2-chloro-9-(2',5'-di-O-benzoyl-β-D-ribofuranosyl)-adenine (E) and 2-chloro-9-(3',5'-di-O-benzoyl-β-D-ribofuranosyl)-adenine (F) by isomerisation To a 1.0 g mixture of 2-chloro-9-(2',5'-di-O-benzoyl-β-D-ribofuranosyl)-adenine (E) (27.4% purity by HPLC) and 2-chloro-9-(3',5'-di-O-benzoyl-β-D-ribofuranosyl)-adenine (F) (47.0% purity by HPLC) was added MeOH (20 mL) and the resulting heterogeneous mixture was stirred at reflux temperature (about 65° C.) for 66 hours. The heterogeneous mixture was cooled to room temperature and filtered and dried providing a 0.62 g of 2-chloro-9-(3',5'-di-O-benzoyl-β-D-ribofuranosyl)-adenine (F) (95.6% purity by HPLC; 126% yield calculated based on compound F, or 80% yield calculated based on compounds E and F in the original mixture). The filtrate contained 1.6% HPLC purity compound F and 5.8% HPLC purity compound E.

Example 3c

Enrichment of 2-chloro-9-(3',5'-di-O-benzoyl-β-D-ribofuranosyl)-adenine (F) from a mixture of 2-chloro-9-(2',5'-di-O-benzoyl-β-D-ribofuranosyl)-adenine (E) and 2-chloro-9-(3',5'-di-O-benzoyl-β-D-ribofuranosyl)-adenine (F) using infrared light A solid mixture of 2-chloro-9-(2',5'-di-O-benzoyl-β-D-ribofuranosyl)-adenine (E) (21.1% by HPLC) and 2-chloro-9-(3',5'-di-O-benzoyl-β-D-ribofuranosyl)-adenine (F) (70.8% by HPLC) was irradiated with infrared light (250 W lamp with 0.5 KW power rating placed about 20 cm from the solid) at about 60° C. (air temperature) for 10.5 h providing a mixture of 2-chloro-9-(2',5'-di-O-benzoyl-β-D-ribofuranosyl)-adenine (E) (17.2% by HPLC) and 2-chloro-9-(3',5'-di-O-benzoyl-β-D-ribofuranosyl)-adenine (F) (78.7% by HPLC) 17.5% 3-OH and 79% 2-OH. The isomerisation reaction was followed by HPLC analysis and the data for samples taken at specific intervals is shown in the table below:

| Time | Compound (E)[a] | Compound (F)[a] |
|---|---|---|
| 0 h | 21.1% | 70.8% |
| 2 h | 20.7% | 71.9% |
| 5 h | 18.2% | 73.7% |
| 10.5 h | 17.2% | 78.7% |

[a]Area percent, as determined by HPLC analysis.

Example 3d

Isomerisation of 2-chloro-9-(3',5'-di-O-benzoyl-β-D-ribofuranosyl)-adenine (F) to a mixture of 2-chloro-9-(2',5'-di-O-benzoyl-β-D-ribofuranosyl)-adenine (E) and 2-chloro-9-(3',5'-di-O-benzoyl-β-D-ribofuranosyl)-adenine (F)

A solution of 0.5 g 2-chloro-9-(3',5'-di-O-benzoyl-β-D-ribofuranosyl)-adenine (F) (90.2% purity by HPLC; containing 4.0% HPLC purity 2-chloro-9-(2',5'-di-O-benzoyl-β-D-ribofuranosyl)-adenine (E)) in sec-butanol (10 mL) at about 100° C. was stirred for 25.5 hours. HPLC analysis of the solution showed it was composed of a mixture of 2-chloro-9-(3',5'-di-O-benzoyl-β-D-ribofuranosyl)-adenine (F) (60.7%) and 2-chloro-9-(2',5-di-O-benzoyl-β-D-ribofuranosyl)-adenine (E) (32.4%). Cooling of the solution to room temperature (about 10° C.) provided 0.3 g of solid after filtration contained 96.8% (HPLC purity) 2-chloro-9-(3',5'-di-O-benzoyl-β-D-ribofuranosyl)-adenine (F).

Example 4

Crystallization of 2-chloro-9-(3',5'-di-O-benzoyl-β-D-ribofuranosyl)-adenine (F)

The crude solid 2-chloro-9-(3',5'-di-O-benzoyl-β-D-ribofuranosyl)-adenine (F) prepared above in EXAMPLE 3a was dissolved in DMSO (825 g, 750 mL) and then MeOH (4118.4 g) was added dropwise at about 20 to 25° C. 30 Minutes later, the heterogeneous mixture was filtered and the filter cake was washed twice with MeOH (332.6 g each) and dried in vacuo at 60° C. for 4 to 6 h. 2-Chloro-9-(3',5'-di-O-benzoyl-β-D-ribofuranosyl)-adenine (F) (199.8 g, 45.2% yield based on 2',3',5'-tri-O-benzoyl-2-chloroadenosine (D) used in Example 2) was obtained with 97.4% HPLC purity, and 2-chloro-9-(2',5'-di-O-benzoyl-β-D-ribofuranosyl)-adenine (E) was 0.05% HPLC purity. $^1$H NMR (300 MHz, $d_6$-DMSO) δ 8.4 (s, 1H), 8.11 (d, J=7.2 Hz), 7.98 (d, J=7.7 Hz), 7.89 (s, 2H), 7.69 (m, 2H), 7.58 (m, 2H), 7.52 (m. 2H), 6.10 (d, J=6.1 Hz, 1H), 6.03 (d, J=6.0 Hz, 1H), 5.70 (dd, J=4.1 Hz, 5 Hz, 1H), 5.13 (dd, J=6.0, 12.0 Hz, 1H), 4.61-4.72 (m, 3H).

Example 5

Preparation of 2-chloro-9-(3',5'-di-O-benzoyl-2'-O-trifluoromethylsulfonyl-β-D-ribofuranosyl)-adenine (G)

To a heterogeneous mixture of crystallized 2-chloro-9-(3',5'-di-O-benzoyl-β-D-ribofuranosyl)-adenine (F) (65 g, purity: 94.7% by A % HPLC, 120.7 mmol) in DCM (650 mL) and pyridine (65 mL) at about 0 to 20° C. under an atmosphere of $N_{2(g)}$ was added Tf$_2$O (85.1 g, 301.6 mmol) dropwise whilst maintaining the temperature within the range of 0 to 20° C. The mixture turned clear and the reaction was deemed complete when the HPLC purity of F was not more than 1%. The mixture was washed with saturated NaHCO$_3$ (325 mL) and the organic phase was washed with 2 N H$_2$SO$_4$ (325 mL) at room temperature The organic phase was dried using 3 Å molecule sieves until the Karl Fischer titration value was <=1000 ppm. The organic phase was evaporated in vacuo at 40° C. until about 290 g of residue (including about 130 mL of DCM) remained. The residue was directly used in the next step. The typical purity of 2-chloro-9-(3',5'-di-O-benzoyl-2'-O-trifluoromethylsulfonyl-β-D-ribofuranosyl)-adenine (G) was >=95% and the yield was >=95%. $^1$H NMR (300 MHz, CDCl$_3$) δ 8.11 (dd, J=8.3, 1.2 Hz, 2H), 7.98 (dd, J=8.3, 1.2 Hz, 2H), 7.87 (s, 1H), 7.70-7.60 (m, 1H), 7.59-7.46 (m, 3H), 7.41 (t, J=7.7 Hz, 2H), 6.34-6.23 (m, 2H), 6.16 (dd, J=5.3, 3.2 Hz, 1H), 6.07 (bs, 2H), 4.86 (dd, J=12.2, 3.3 Hz, 1H), 4.81-4.74 (m, 1H), 4.65 (dd, J=12.2, 4.2 Hz, 1H).

Example 6

Preparation of 2-chloro-9-(3',5'-di-O-benzoyl-2'-deoxy-2'-fluoro-β-D-arabinofuranosyl)-adenine (H)

To the residue of 2-chloro-9-(3',5-di-O-benzoyl-2'-O-trifluoromethylsulfonyl-β-D-ribofuranosyl)-adenine (G) prepared above was charged EtOAc (697.5 g) and guanidine carbonate (87 g, 482.9 mmol) at room temperature and the mixture was heated to 60° C. 3HF.Et$_3$N (116.7 g, 723.9 mmol) was added dropwise into the mixture (over a 0.5 to 1 h period) then the mixture was heated under reflux (80° C.) until the HPLC purity of compound G was not more than 3% (required about 10 h). The reaction mixture was cooled to below 35° C. and saturated NaHCO$_3$ (775 mL) was added dropwise. The mixture was filtered to assist phase separation and the aqueous phase was extracted with EtOAc (232.5 mL). The combined organic phase was evaporated in vacuo at 40° C. until there was about 200 g (including about 150 mL of EtOAc) of residue remaining. The residue was dissolved in MeOH (450 mL) under reflux and was then hot filtrated. The filtrate was cooled to allow precipitation, and was kept at about 50° C. for another 2 h. The heterogeneous mixture was cooled to about 20 to 25° C. over a 2 h period and was then kept at this temperature for 6 h. The heterogeneous mixture was filtered and the filter cake was washed twice with MeOH (50 mL each). The solid was dried in vacuo at 60° C. for about 4 to 6 h to give 2-chloro-9-(3',5'-di-O-benzoyl-2'-deoxy-2'-fluoro-β-D-arabinofuranosyl)-adenine (H) with a HPLC purity of 98% along with <=0.10% purity of 2-chloro-9-(3',5'-di-O-benzoyl-2'-deoxy-2'-chloro-β-D-arabinofuranosyl)-adenine (J). The 2-chloro-9-(3',5'-di-O-benzoyl-2'-deoxy-2'-fluoro-β-D-arabinofuranosyl)-adenine (H) was recrystallized from a mixture of EtOAc and MeOH (1:3 v/v, 600 mL) to further reduce total purity of 2-chloro-9-(2',3',5'-tri-O-benzoyl-β-D-arabinofuranosyl)-adenine and 2-chloro-9-(2'-O-acetyl-3',5'-di-O-benzoyl-β-D-arabinofuranosyl)-adenine to not more than 0.15%. The yield was 44.4% based on 2-chloro-9-(3',5'-di-O-benzoyl-β-D-ribofuranosyl)-adenine (F). $^1$H NMR (300 MHz, CDCl$_3$) δ 8.0-8.1 (m, 5H), 8.0 (s, 1H), 7.3-7.6 (m, 5H), 6.61 (t, J=2.85 Hz, 1H), 6.54 (d, J=2.4 Hz, 2H), 5.75 (dd, J=2.1, 17.1 Hz, 1H), 5.37 (dd, J=2.7 Hz, 49.8 Hz, 1H), 4.81 (d, J=4.2 Hz, 1H), 4.57 (m, 1H).

Example 7

Preparation of 2-chloro-9-(2'-deoxy-2'-fluoro-β-D-arabinofuranosyl)-adenine (clofarabine)

A mixture of 2-chloro-9-(3',5'-di-O-benzoyl-2'-deoxy-2'-fluoro-β-D-arabinofuranosyl)-adenine (H) (5 g) and 29% MeONa/MeOH (0.11 g) in MeOH (75 mL) was stirred at between 30 to 40° C. until the reaction was complete (within about 1-3 h). AcOH (0.035 g) was added and the mixture was evaporated at 30 to 40° C. in vacuo until there is about 25 g (including about 5 volumes of MeOH) of heterogeneous mixture remaining. The mixture was cooled to 0 to 20° C. and after 2 h was filtered. The filter cake was washed twice with MeOH (5 mL each) and dried in vacuo at 60° C. to give 2.6 g of clofarabine as a white solid with 99.8% HPLC purity in 86.7% yield based on compound H. The crude clofarabine (2.6 g) was dissolved in water (104 mL) at about 80° C. and was hot filtered at about 70-80° C. The filtrate was slowly cooled to crystallize the clofarabine and was stirred at room temperature overnight. The mixture was filtered, washed with MeOH (5.2 mL) and dried in vacuo to give clofarabine (2.1 g) in ca. 80% yield with 99.8% HPLC purity. $^1$H NMR (300 MHz, d$_6$-DMSO) δ 8.27 (dd, 1H, H8, J=1.8 Hz), 6.33 (dd, J=4.8 Hz, J=13.8 Hz, 1H), 5.95 (d, J=5.1 Hz, 1H), 5.21 (dt, J=4.2 Hz, J=52.8 Hz, 1H), 5.08 (t, J=5.7 Hz, 1H), 4.42 (dq, J=19.1 Hz, 1H), 3.83 (m, J=5.1 Hz, 1H), 3.65 (m, J=6.0 Hz, J=11.7 Hz, 2H).

The references discussed above are:

[1] Wright J. A., Taylor N. F. and Fox J. J. *J. Org. Chem.* 1969, 34 (9), 2632-2636.

[2] Anderson C. D., Goodman L. and Bake B. R. *J. Amer. Chem. Soc.* 1958, 80 (19), 5247-5252.

[3] Watanable K. A., Chu C. K. and Fox J. J. (Sloan-Kettering Institute for Cancer Research), U.S. Pat. No. 4,751,221 (1988).

[4] Reichman U., Watanabe K. A. and Fox J. J., *Carbohydr. Res.* 1975, 42, 233-240.

[5] Montgomery J. A., Shortnacy A. T., Carson D. A. and Secrist J. A., *J. Med. Chem.* 1986, 29, 2389-2392.

[6] Howell H. G., Brodfuehrer P. R., Brundidge S. P., Sapino C. J., *J. Org. Chem.* 1985, 50, 2597-2598; Tann C. H., Brodfuehrer P. R., Brundidge S. P., Sapino C. J. and Howell H. G., *J. Org. Chem.* 1985, 50, 3644-3647.

[7] Tann C. H., Brodfuehrer P. R., Brundidge S. P., Sapino C. J. and Howell H. G. *J. Org. Chem.* 1985, 50, 3644-3647; Howell H. G., Brodfuehrer P. R., Brundidge S. P., Benigni D. A. and Sapino C. J., *J. Org. Chem.* 1988, 53, 85-88.

[8] Montgomery, J. A., Shortnacy-Fowler, A. T., Clayton, S. D., Riordan, J. M. and Secrist III, J. A., *J. Med. Chem.* 1992, 35, 397-401; Montgomery J. A. and Secrist J. A. (Southern Research Institute), WO 9014352 A1 and U.S. Pat. No. 5,034,518.

[9] Montgomery J. A., Fowler A. T., Secrist, III, J. A., (Southern Research Institute), U.S. Pat. No. 6,949,640 (2005) and U.S. Pat. No. 7,470,784 (2008).

[10] Bauta W. E., Schulmeier B. E., Puente J. F., Cantrell W. R., Jr., Lovett D., Goebel J., Anderson B., Ionescu D. and Guo R., *Org. Proc. Res. Dev.,* 2004, 8, 889-896; William E. B., Burke B. D., Schulmeier B. E., Cantrell W. R., Jr., Lovett D., Puente J. (ILEX Products, Inc.), U.S. Pat. No. 6,680,382 (2004).

[11] Ishido Y., Nakazaki N. and Sakairi N., J. C. S., *Perkin Trans. I,* 1979, 2088-2098.

[12] Ishido Y., Sakairi N., Okazaki K., and Nakazaki N., J. C. S., *Perkin Trans. I,* 1980, 563-573.

[13] Sakairi N, Rahman, Md. D, Tamaki K., and Ishido Y., *Nucleosides & Nucleotides,* 1982, 1, 99-110.

[14] Ishido Y., Sakairi N, and Hirao I., *Nucleic Acids Research,* Special publication No. 5, 1978, s263-265.

[15] Bauman J. G. and Wirsching R. C. (Schering Aktiengesellschaft, Berlin), U.S. Pat. No. 5,602,246 (1997).

[16] McClinton, M. A., *Aidrichimica Acta,* 1995, 28, 31-35.

[17] Yoneda, N., *Tetrahedron,* 1991, 47, 5329-5365.

What is claimed is:

1. A process comprising:

mixing guanidine carbonate, a fluorinating agent that is a source of fluoride ions, and a compound of formula VII

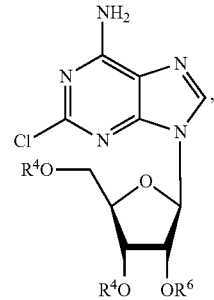

wherein each $R^4$ is independently a hydroxyl protecting group, $OR^6$ is a leaving group to obtain a compound of formula VIII:

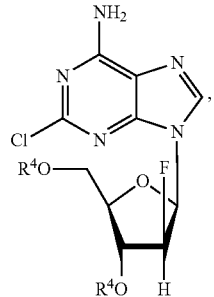

wherein $R^4$ is as defined above.

2. The process of claim 1 further comprising a step of deprotecting the compound of formula VIII to obtain clofarabine of formula I

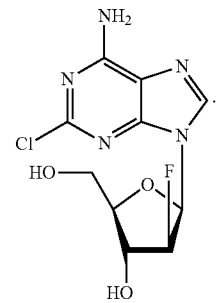

3. The process of claim 2, wherein the compound of formula VIII applied in the deprotecting step comprises no greater than 0.10% peak area as determined by high performance liquid chromatography (HPLC) analysis of a compound of formula IX:

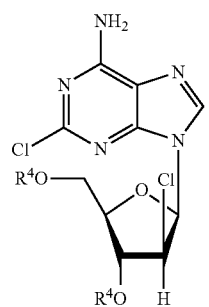

IX

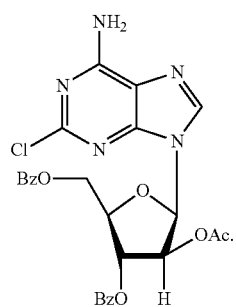

Y wherein R⁴ is as defined above in claim 1.

4. The process of claim 2 wherein the compound of formula VIII to be deprotected has a HPLC purity of at least 99% (peak area).

5. The process of claim 2 wherein the compound of formula VIII to be deprotected contains a no greater than 0.1% peak area of a compound of formula J by HPLC analysis of the compound of formula VIII, no greater than 0.1% peak area of a compound of formula X by HPLC analysis of the compound of formula VIII, no greater than 0.1% peak area of a compound of formula Y by HPLC analysis of the compound of formula VIII, and no greater than 0.15% peak areas of the total amount of the compound of X and the compound of formula Y by HPLC analysis of the compound of formula VIII:

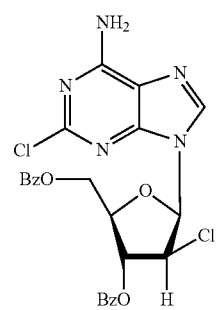

J

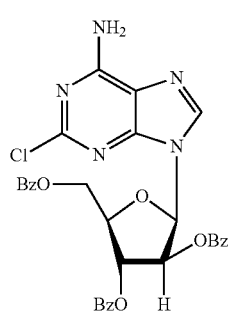

X

6. The process of claim 1 wherein the fluorinating agent is HF or a mixture of HF and an organic Lewis base.

7. The process of claim 6 wherein the organic Lewis base is an amine.

8. The process of claim 1 further comprising derivatizing a compound of formula (V)

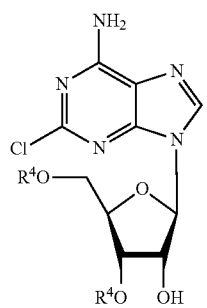

V wherein R⁴ is as defined above in claim 1 to prepare the compound of formula VII.

9. The process of claim 8 further comprising:

1) partially deprotecting a compound of formula (IV):

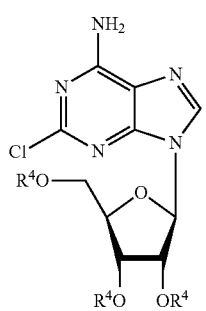

IV to obtain a first reaction mixture comprising the compound of formula (V) and a compound of formula (VI)

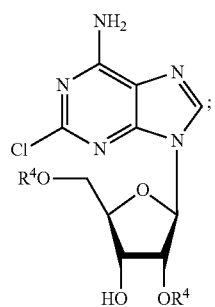

VI 2) isomerizing the compound of formula VI in the mixture obtained in step 1) to the compound of formula V in a solvent at an elevated temperature to obtain a second reaction mixture; and
3) isolating the compound of formula (V) from second reaction mixture.

10. The process of claim 9 further comprising: coupling a protected ribofuranose of formula

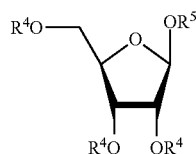

III wherein $R^4$ is as defined above, $OR^5$ is a leaving group, with a silylated 2-chloroadenine of formula II:

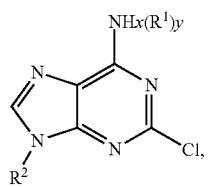

II wherein $R^1$ is $Si(R^3)_3$, $R^2$ is hydrogen or $R^1$, $R^3$ is alkyl, alkenyl, alkynyl, aryl or heteroaryl and contains 1 to 20 carbon atoms, and x is 0 or 1 whilst y is 2 or 1, respectively, in the presence of a Lewis acid or a Brønsted acid, to form the compound of formula (IV).

11. The process of claim 1 wherein the fluorinating agent is selected from the group consisting of KF, $KHF_2$, CsF, tetrabutylammonium fluoride (TBAF), and $3HF \cdot Et_3N$.

12. A process comprising:
1) mixing a solvent and a compound of formula VI

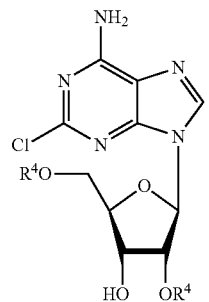

VI wherein each $R^4$ is independently a hydroxy protecting group, to obtain a first mixture;

2) heating the first mixture of step 1) for a sufficient period of time so that a substantial amount of the compound of formula VI is isomerized to a compound of formula (V)

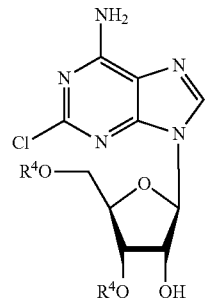

V wherein each $R^4$ is as defined above, to obtain a second mixture comprising the compound of formula (VI) and the compound of formula (V); and 3) isolating the compound of formula (V) from the second mixture to obtain an isolated compound of formula (V) and a third mixture comprising the compound of formula (VI).

13. The process of claim 12 wherein the heating step is carried out for at least 5 hours.

14. The process of claim 12 wherein the solvent is selected so that the first mixture is heterogeneous during the heating step, the compound of formula (V) is substantially less dissolved in the solvent than the compound of formula (VI) during the heating step, but the compound of formula (V) is sufficiently insoluble, and the compound of formula (VI) is sufficiently soluble in the solvent when the elevated temperature is lowered to effect the isolation of the compound of formula (V) by selective crystallization.

15. The process of claim 12 wherein during the heating step, the first mixture is heterogeneous, and the compound of formula (VI) is isomerized to the compound of formula (V) until the level of the compound of formula (VI) in the solution phase of the second mixture reaches a steady state.

16. The process of claim 12 wherein the solvent is selected so that the first mixture is in form of a homogenous solution during the heating step, but the compound of formula (V) is substantially insoluble, and the compound of formula (VI) is substantially soluble in the solvent when the elevated temperature is lowered to effect the isolation of the compound of formula (V) by selective crystallization.

17. The process of claim 12 wherein the solvent is selected from the group consisting of a lower alcohol ($C_1$-$C_6$), DMSO, and combinations thereof.

18. The process of claim 12 wherein the first mixture when heated is in form of a homogenous solution, and the process comprises repeating at least once the steps 1)-3) to process the third mixture.

19. The process of claim 12 wherein the first mixture is heated to a temperature of about 35° C. to 120° C.

20. The process of claim 12 wherein the first mixture is heated to the reflux temperature of the solvent.

21. The process of claim 12 further comprising:
derivatizing the compound of formula (V) to prepare a compound of formula VII:

43

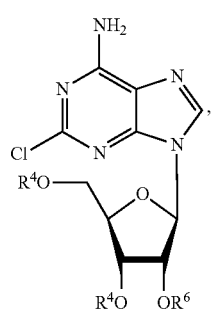

VII wherein each $R^4$ is as defined in claim 12, and $OR^6$ is a leaving group;

mixing guanidine carbonate, a fluorinating agent that is a source of fluoride ions, and the compound of formula VII to obtain a compound of formula VIII:

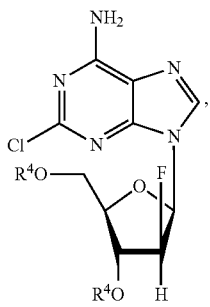

VIII wherein $R^4$ is as defined above; and
deprotecting the compound of formula VIII to obtain clofarabine of formula I

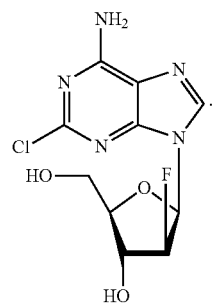

I

44

22. The process of claim 12 further comprising a step of recrystallizing the isolated compound of formula (V) from at least one solvent such that the amount of residual acetic acid in the recrystallized compound of formula (V) is controlled to no more than 0.5 weight percent by gas chromatographic (GC) analysis.

23. The process of claim 22 wherein the at least one solvent is a mixture of DMSO and MeOH.

24. A process comprising:
1) irradiating a compound of formula VIb in a solid form

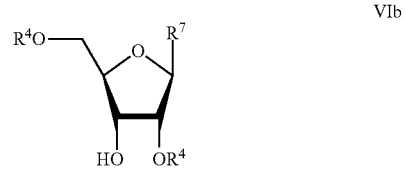

VIb wherein each $R^4$ is benzoyl and $R^7$ is 2-chloro-adenin-9-yl with electromagnetic radiation so that at least partial amount of the compound of formula VIb is isomerized to a compound of formula (Vb)

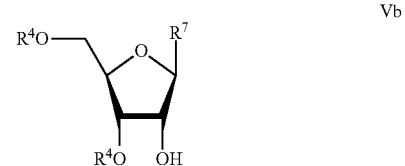

Vb wherein each $R^4$ and $R^7$ are as defined above; and
2) isolating the compound of formula (Vb) from the compound of formula (VIb).

25. The process of claim 24 wherein the electromagnetic radiation is infrared radiation.

\* \* \* \* \*